US005968981A

United States Patent [19]
Chien et al.

[11] Patent Number: 5,968,981
[45] Date of Patent: Oct. 19, 1999

[54] RETINOID SUPPRESSION OF VENTRICULAR MUSCLE CELL HYPERTROPHY

[75] Inventors: Kenneth R. Chien, La Jolla, Calif.; Ming Dong Zhou, Darlinghurst, Australia

[73] Assignee: The Regents of the University of California, Calif.

[21] Appl. No.: 09/037,765

[22] Filed: Mar. 10, 1998

Related U.S. Application Data

[62] Division of application No. 08/685,339, Jul. 22, 1996, Pat. No. 5,767,155
[60] Provisional application No. 60/019,016, Jul. 28, 1995.

[51] Int. Cl.⁶ ........................... A61K 31/19; A61K 31/07
[52] U.S. Cl. ........................................... 514/557; 514/725
[58] Field of Search ..................................... 514/557, 725

[56] References Cited

U.S. PATENT DOCUMENTS

| | | | |
|---|---|---|---|
| 5,344,644 | 9/1994 | Igari et al. | 424/85.1 |
| 5,767,155 | 6/1998 | Chien et al. | 514/557 |

OTHER PUBLICATIONS

Argentin, Stefania, et al., "Distal cis–Acting Promoter Sequences Mediate Glucocorticoid Stimulation of Cardiac Atrial Natriuretic Factor Gene Transcription," *J. Biol. Chem.*, (Dec. 5, 1991) vol. 266, No. 34, pp. 23315–23322.
Argentin, Stefania, et al., "The Gene for Rat Atrial Natriuretic Factor," *J. Biol. Chem.*, (Apr. 25, 1985), vol. 260, No. 8, pp. 4568–4571.
Battistini, Bruno, et al., "Growth Regulatory Properties of Endothelins," *Peptides,* (1993) vol. 14, pp. 385–399.
Buttrick, Peter, et al., "Effects of chronic dobutamine on cardiac mechanics and biochemistry after myocardial infarction in rats," *Am. J. Physiol.* (1991), pp. H473–H479.
Cherrington, Julie M., et al., "Human Cytomegalovirus ie1 Transactivates the α Promoter–Enhancer via an 18–Base–Pair Repeat Element," *J. Virol.* (Mar. 1989), vol. 63, No. 3, pp. 1435–1440.
Chien, Kenneth R., et al., "Regulation of cardiac gene expression during myocardial growth and hypertrophy: molecular studies of an adaptive physiologic response," *FASEB,* Dec. 1991, vol. 5, pp. 3037–3046.
Chirgwin, John M., et al., "Isolation of Biologically Active Ribonucleic Acid from Sources Enriched in Ribonuclease," *Biochemistry,* (1979) vol. 18, No. 24, pp. 5294–5299.
Cox, Lydia R., et al., "Effects of retinoic acid on NIH3T3 cell transformation by the H–ras oncogene," *J. Cancer Res. Clin. Oncol.,* (1991) vol. 117, pp. 102–108.
Damm, Klaus, et al., "Functional inhibition of retinoic acid response by dominant negative retinoic acid receptor mutants," *Proc. Natl. Acad. Sci. USA,* (Apr. 1993) vol. 90, pp. 2989–2993.
De Wet, Jeffrey, R., et al., "Firefly Luciferase Gene: Structure and Expression in Mammalian Cells," *Mol. Cell. Biol.,* (Feb. 1987) vol. 7, No. 2, pp. 725–737.

Dyson, E. et al., "Atrial–like Phenotype Is Associated With Embryonic Ventricular Failure In Retinoid X Receptor α –/–mice" *Proc. Natl. Acad. Sci. USA* (Aug. 1995) vol. 92, pp. 7386–7390.
Evans, Ronald, M., "The Steroid and Thyroid Hormone Receptor Superfamily," *Science ,* (May 13, 1988) vol. 240, pp. 889–895.
Geenen, David L., "Papillary mechanics and cardiac morphology of infarcted rat hearts after training," *J. Appl. Physiol.* (1987) pp. 92–96.
Giguere, Vincent, et al., "Identification of a Novel Isoform of the Retinoic Acid Receptor γ Expressed in the Mouse Embryo," *Mol. Cell. Biol.,* (May 1990) vol. 10, No. 5, pp. 2335–2340.
Giguere, Vincent, et al., "Identification of a receptor for the morphogen retinoic acid," *Nature,* (Dec. 17, 1987), vol. 330, pp. 624–629.
Glembotski, Christopher C., "The Characterization of Atrial Natriuretic Peptide (ANP) Expression by Primary Cultures of Atrial Myocytes Using an ANP–Specific Monoclonal Antibody and an ANP Messenger Ribonucleic Acid Probe," *Endocrinology,* (1987) vol. 121, No. 3, pp. 843–852.
Gossett, Lani A., et al., "A New Moyocyte–Specific Enhancer–Binding Factor That Recognizes a Conserved Element Associated with Multiple Muscle–Specific Genes," *Mol. Cel. Biol.,* (Nov. 1989) vol. 9, No. 11, pp. 5022–5033.
Grepin, Claudine, et al., "A Hormone–Encoding Gene Identifies a Pathway for Cardiac but Not Skeletal Muscle Gene Transcription," *Mol. Cell. Biol.,* (May 1994) vol. 14, No. 5, pp. 3115–3129.
Hermann, Thomas, et al., "Heterodimeric Receptor Complexes Determine 3,5,3'–Triidothyronine and Retinoid Signaling Specificities," *Mol. Endocrinol.,* (1992) vol. 6, No. 7, pp. 1153–1162.
Heyman, Richard A., et al., "9–Cis Retinoic Acid is a High Affinity Ligand for the Reinoid X Receptor," *Cell ,* (Jan. 24, 1992), vol. 68, pp. 397–406.
Hilal–Dandan, Randa, et al., "Coupling of the Type A Endothelin Receptor to Multiple Responses in Adult Rat Cardiac Myocytes," *Mol. Pharm.,* (1994) vol. 45, pp. 1183–1190.
Ihara, Masaki, et al., "Biolgcial Profiles of Highly Potent Novel Endothelin Antagonists Selective for the $ET_A$ Receptor," *Life Sciences,* (1992) vol. 50, No. 4, pp. 247–255.
Inoue, Akihiro, et al., "The human endothelin family: Three structurally and pharmacologically distinct isopeptides predicted by three separate genes," *Proc. Natl. Acad. Sci. USA,* (Apr. 1989) vol. 86, pp. 2863–2867.

(List continued on next page.)

*Primary Examiner*—Kevin E. Weddington
*Attorney, Agent, or Firm*—Carol L. Francis; Bozicevic, Field & Francis LLP

[57] ABSTRACT

A method of suppressing ventricular muscle cell hypertrophy induced by an $\alpha_1$-adrenergic agonist or endothelin, by providing an effective amount of a retinoic acid compound. Also provided are methods for identifying compounds which suppress ventricular muscle cell hypertrophy, compounds which inhibit the retinoic acid suppression of ventricular muscle cell hypertrophy, and therapeutic methods.

13 Claims, 4 Drawing Sheets

OTHER PUBLICATIONS

Ito, Hiroshi, et al., "Endothelin–1 induces Hypertrophy With Enhanced Expression of Muscle–Specific Genes in Cultured Neonatal Rat Cardiomyocytes," *Circ. Res.,* (Jul. 1991) vol. 69, No. 1, pp. 209–215.

Jones, Linda G., et al., "Endothelin stimulates multiple responses in isolated adult ventricular cardiac myocytes," *Am. J. Physiol.,* (1992) vol. 263, pp. H1447–H1454.

Jong, Ling, et al., "Conformational Effects on Retinoid Receptor Selectively, 1. Effect of a 9–Double Bond Geometry on Retinoid X Receptor Activity," *J. Med. Chem.,* (1993) vol. 36, pp. 2605–2613.

Kelly, Tamsin Lisa, et al., "Prediction of outcome in late–stage cardiomyopathy," *Amer. Heart J.* (May 1990) vol. 119, No. 5, pp. 1111–1121.

Knowlton, Kirk U., et al., "Co–regulation of the Atrial Natriuretic Factor and Cardiac Myosin Light Chain–2 Genes during α–Adrenergic Stimulation of Neonatal Rat Ventricular Cells," *J. Biol. Chem.,* (Apr. 25, 1991) vol. 266, No. 12, pp. 7759–7768.

Knowlton, Kirk U., et al., "The $\alpha_{1A}$–Adrenergic Receptor Subtype Mediates Biochemical, Molecular, and Morphologic Features of Cultured Myocardial Cell Hypertrophy," *J Biol Chem.,* (Jul. 25, 1993) vol. 268, No. 21, pp. 15374–15380.

Kloner, Robert A., et al., "The effect of early exercise on myocardial infarct scar formation," *Amer. Heart J.* (Nov. 1983) vol. 106, No. 5, Part 1, pp. 1009–1013.

Kumar, C. Chandra, et al., "Heart Myosin Light Chain 2 Gene," *J. Biol. Chem.,* (Feb. 25, 1986) vol. 261, No. 6, pp. 2866–2872.

LaMorte, Vicki J., et al., "$G_q$—and Ras–dependent Pathways Mediate Hypertrophy of Neonatal Rat Ventricular Myocytes following $\alpha_1$–Adrenergic Stimulation," *J. Biol. Chem.,* (May 6, 1994) vol. 269, No. 18, pp. 13490–13496.

Leder, Aya, et al., "v–Ha–ras transgene abrogates the initiation step in mouse skin tumorigenesis: Effects of phorbol esters and retinoic acid," *Proc. Natl. Acad. Sci. USA* (Dec. 1990), vol. 87, pp. 9178–9182.

Mangelsdorf, David J., et al., "Nuclear receptor that identifies a novel retinoic acid response pathway," *Nature* (May 17, 1990), vol. 345, pp. 224–229.

Mangelsdorf, David J., et al., "A Direct Repeat in the Cellular Retinol–Binding Protein Type II Gene Confers Differential Regulation by RXR and RAR," *Cell* (Aug. 9, 1991), vol. 66, pp. 555–561.

Mangelsdorf, David J., et al., "Characterization of three RXR genes that mediate the action of 9–cis retinoic acid," *Genes & Dev.* (1992) vol. 6, pp. 329–344.

Monge, J.C. et al., (1995) "Differentiation of Embryonal Carcinoma Cells to a Neural or cariomyocyte Lineage Is Associated with Selective Expression of Endothelin Receptors", *J. Biol. Chem.,* 270(25):15385–90.

Rohrer, Daniel K., et al., "Influence of Thyroid Hormone and Retinoic Acid on Slow Sarcoplasmic Reticulum $Ca^{2+}$ ATPase and Myosin Heavy Chain α Gene Expression in Cardiac Myocytes," *J. Biol. Chem.,* (May 5, 1991) vol. 266, No. 13, pp. 8638–8646.

Rosenthal, Nadia, "Identification of Regulatory Elements of Cloned Genes with Functional Assays," *Methods Enzymol.* (1987) vol. 152, pp. 704–720.

Salbert, Gilles, et. al., "Retinoic Acid Receptors and Retinoid X Receptor–α Down–Regulate the Transforming Growth Factor–$\beta_1$ Promoter by Antagonizing AP–1 Activity," *Molec. Endocrinol.* (1993) vol. 7, No. 10, pp. 1347–1356.

Schule, Roland, et al., "Retinoic acid is a negative regulator of AP–1–responsive genes," *Proc. Natl. Acad. Sci. USA,* (Jul. 1991) vol. 88, pp. 6092–6096.

Shubeita, Huda E., et al., "Endothelin Induction of Inositol Phospholipid Hydrolysis, Sarcomere Assembly, and Cardiac Gene Expression in Ventricular Myocytes," *J. Biol. Chem.* (Nov. 25, 1990) vol. 265, No. 33, pp. 20555–20562.

Simpson, Paul, et al., "Myocyte Hypertrophy in Neonatal Rat Heart Cultures and Its Regulation by Serum and by Catecholamines," *Circulation Res.,* (Dec. 1982) vol. 51, No. 6, pp. 787–801.

Sucov, Henry M., et al., "RXRα mutant mice establish a genetic basis for vitamin A signaling in heart morphogenesis," *Genes & Dev.,* (1994) vol. 8, pp. 1007–1018.

Sucov, Henry M., et al., "Characterization of an autoregulated response element in the mouse retinoic acid receptor type βgene," *Proc. Natl. Acad. Sci. USA,* (Jul. 1990) vol. 87, pp. 5392–5396.

Suzuki, Takahiko, et al., "Endothelin–1 Stimulates Hypertrophy and Contractility of Neonatal Rat Cardiac Myocytes in a Serum–Free Medium. II," *J. Cariovasc. Pharmacol.,* (1991) vol. 17 (Suppl. 7), pp. S182–S186.

Thorburn, Andrew, et al., "HRas–dependent Pathways Can Activate Morphological and Genetic Markers of Cardiac Muscle Cell Hypertrophy," *J. Biol. Chem.* (Jan. 25, 1993) vol. 268, No. 3, pp. 2244–2249.

Umesono, Kazuhiko, et al., "Direct Repeats as Selective Response Elements for the Thyroid Hormone, Retinoic Acid, and Vitamin $D_3$ Receptors," *Cell* (Jun. 28, 1991) vol. 65, pp. 1255–1266.

Webb, Marie L., et al., "The Endothelin Receptor Antagonist, BQ–123, Inhibits Angiotensin II–Induced Contractions in Rabbit Aorta," *Biochem. Biophys. Res. Commun.,* (Jun. 30, 1992) vol. 185, No. 3, pp. 887–892.

Wei, Chi–Ming, et al., "Endothelin in Human Congestive Heart Failure," *Circulation* (Apr. 1994), vol. 89, No. 4, pp. 1580–1586.

Yanagisawa, Masashi, et al., "Molecular biology and biochemsitry of the endothelins," *TIPS* (Sep. 1989) vol. 10, pp. 374–378.

Zhang, Xiao–kun, et al., "Homodimer formation of retinoid X receptor induced by 9–cis retinoic acid," *Nature* (Aug. 13, 1992) vol. 358, pp. 587–591.

Zhang, Xiao–kun, et al., "Retinoid X receptor is an auxilliary protein for thyroid hormone and retinoic acid receptors," *Nature,* (Jan. 30, 1992), vol. 355, ppp. 441–446.

Wu, et al., "1,25$(OH)_2D_3$ Suppresses Expression and Secretion of Atrial Natriuretic Peptide from Cardiac Myocytes," *American Physiological Society* (1995), 268 (*Endocrinol. Metab.* ): E1108–E1113.

Zhou et al., Retinoid–dependent pathways supports myocardial cell hypertrophy, (1995).

RETINOID SUPPRESSION OF VENTRICULAR MUSCLE CELL HYPERTROPHY

CROSS-REFERENCE TO RELATED APPLICATION

This application is a divisional of U.S. application Ser. No. 08/685,339, filed Jul. 22, 1996, now U.S. Pat. No. 5,767,155 which application is related to earlier filed copending provisional application Ser. No. 60/019,016, filed Jul. 28, 1995, which application is incorporated herein by reference.

STATEMENT AS TO FEDERALLY SPONSORED RESEARCH

This invention was supported in part by National Cancer Institute grants CA54418, HD27183, NHLBI grants HL45069, HL53773, HL46345, and 91-022170. The U.S. Government may have rights in this invention.

TECHNICAL FIELD

This invention relates to compounds which affect ventricular muscle cell hypertrophy, an assay for identifying such compounds, and to methods for modulating cardiac function in the treatment of heart disorders.

BACKGROUND OF THE INVENTION

Heart failure affects approximately three million Americans, developing at a rate of approximately 400,000 new cases per year. Current therapy for heart failure is primarily directed to using angiotensin-converting enzyme (ACE) inhibitors and diuretics. ACE inhibitors appear to slow the progression towards end-stage heart failure in patients; however, they are unable to relieve symptoms in more than 60% of heart failure patients and reduce mortality of heart failure only by approximately 15–20%. Heart transplantation is limited by the availability of donor hearts. With the exception of digoxin, the chronic administration of positive inotropic agents has not resulted in a useful drug without accompanying adverse side effects, such as increased arrhythmia, sudden death, or other deleterious side effects related to survival. These deficiencies in current therapy suggest the need for additional therapeutic approaches.

Cardiac muscle hypertrophy is one of the most important adaptive physiological responses of the myocardium. In response to increased demands for cardiac work or following a variety of pathological stimuli which lead to cardiac injury, the heart adapts through the activation of a hypertrophic response in individual cardiac muscle cells, which is characterized by an increase in myocyte size, the accumulation of contractile proteins within individual cardiac cells, the activation of embryonic gene markers expression, and the lack of a concomitant effect on muscle cell proliferation. Although the hypertrophic process can initially be compensatory, there can be a pathological transition in which the myocardium becomes dysfunctional (Braunwald (1994) in *Pathophysiology of Heart Failure*, (Braunwald, ed.); Saunders, Philadelphia; Vol. 14, pp 393–402).

Studies in an in vitro model system of ventricular muscle cell hypertrophy have led to the identification of a number of mechanical, hormonal, growth factor, and pathological stimuli which can activate several independent features of hypertrophy (Chien et al. (1991) FASEB J. 5:3037–3046; Knowlton et al. (1991) J. Biol. Chem. 266:7759–7768; Shubeita et al. (1990) J. Biol. Chem. 265:20555–20562; Thorburn et al. (1993) J. Biol. Chem. 268:2244–2249; LaMorte et al. (1994) J. Biol. Chem. 269:13490–13496; Knowlton et al. (1993) J. Biol. Chem. 268:15374–15380). Currently, there are at least two signal transduction pathways, involving both ras- (Thorburn et al. (1993) supra), and $G_q$ protein-dependent downstream effectors (LaMorte et al. (1994) supra) implicated in the activation of features of the hypertrophic response in the in vitro model system. While a great deal of progress has been made in uncovering the signaling pathways which activate the ventricular muscle cell hypertrophic response, relatively little is known as to the mechanisms which might inhibit or suppress the hypertrophic response.

While progress has been made in uncovering the signaling pathways which activate the ventricular muscle cell hypertrophic response, relatively little is known as to mechanisms which inhibit or suppress the hypertrophic response.

There is a need for an improved heart failure therapy, such as congestive heart failure and hypertrophic cardiomyopathy.

SUMMARY OF THE INVENTION

The present invention is based in part on the discovery that retinoic acid suppresses $\alpha_1$-adrenergic agonist- and endothelin-mediated ventricular muscle cell hypertrophy. Accordingly, the invention features a method of suppressing ventricular muscle cell hypertrophy by contacting ventricular muscle cells with an effective amount of a retinoic acid compound, retinoic acid derivative, or pharmaceutical salt thereof.

The invention features a method of identifying compounds which suppress ventricular muscle cell hypertrophy, comprising contacting ventricular muscle cells with a test compound in the presence of an inducer of ventricular muscle cell hypertrophy, and measuring the development of ventricular muscle cell hypertrophy.

The development of hypertrophy in ventricular muscle cells is measured in cells exposed to an inducer of ventricular muscle cell hypertrophy with and without the test compound, and the development of hypertrophy compared. The development of ventricular muscle cell hypertrophy is measured in a variety of ways, including by increase in cell size, induction of a genetic marker of ventricular muscle cell hypertrophy, increase in the assembly of an individual contractile protein such as myosin light chain-2v (MLC-2v) into organized contractile units, accumulation of contractile units, activation of a program of immediate early gene expression, and the induction of genes encoding contractile and embryonic proteins. In a specific embodiment, ventricular muscle cell hypertrophy is measured by determining the expression of an atrial-marker, for example, atrial natriuretic factor (ANF).

In one embodiment of the method of identifying compounds which suppress ventricular muscle cell hypertrophy, cells are incubated with an inducer of $\alpha_1$-adrenergic-mediated hypertrophy with and without the test compound, and the ability of the test compound to suppress development of $\alpha_1$-adrenergic-mediated ventricular muscle cell hypertrophy measured. In another embodiment, the cells are incubated with an endothelin with and without the test compound, and the ability of the test compound to suppress endothelin-mediated ventricular muscle cell hypertrophy determined. A test compound which suppresses ventricular muscle cell hypertrophy may block a hypertrophic pathway in a variety of ways, including by activating retinoic acid-specific receptors, e.g., RAR.

The invention features a method for identifying compounds which inhibit retinoic acid suppression of ventricular muscle cell hypertrophy. A compound may inhibit retinoic acid suppression of ventricular muscle cell hypertrophy by blocking, suppressing, reversing, or antagonizing the action of the retinoic acid action. In one embodiment, cells are incubated with an inducer of ventricular muscle cell hypertrophy in the presence of a retinoic acid compound that suppresses the development of ventricular muscle cell hypertrophy, and with and without the test compound, and the ability of the test compound to block the retinoic acid compound suppression of ventricular muscle cell hypertrophy is measured. The inducer of ventricular muscle cell hypertrophy may be an $\alpha_1$-adrenergic agonist or endothelin.

The invention features a therapeutic method for treatment or prevention of ventricular muscle cell hypertrophy-mediated heart failure in a mammal comprising administering an therapeutically effective amount of a retinoic acid compound. In one embodiment, the therapeutic method of treating heart failure includes treating or preventing $\alpha_1$-adrenergic-mediated ventricular muscle cell hypertrophy. In another embodiment, the therapeutic method treats or prevents endothelin-mediated ventricular muscle cell hypertrophy.

Other aspects of the invention will become apparent from the following detailed description and the claims.

DETAILED DESCRIPTION

Figure 1A:
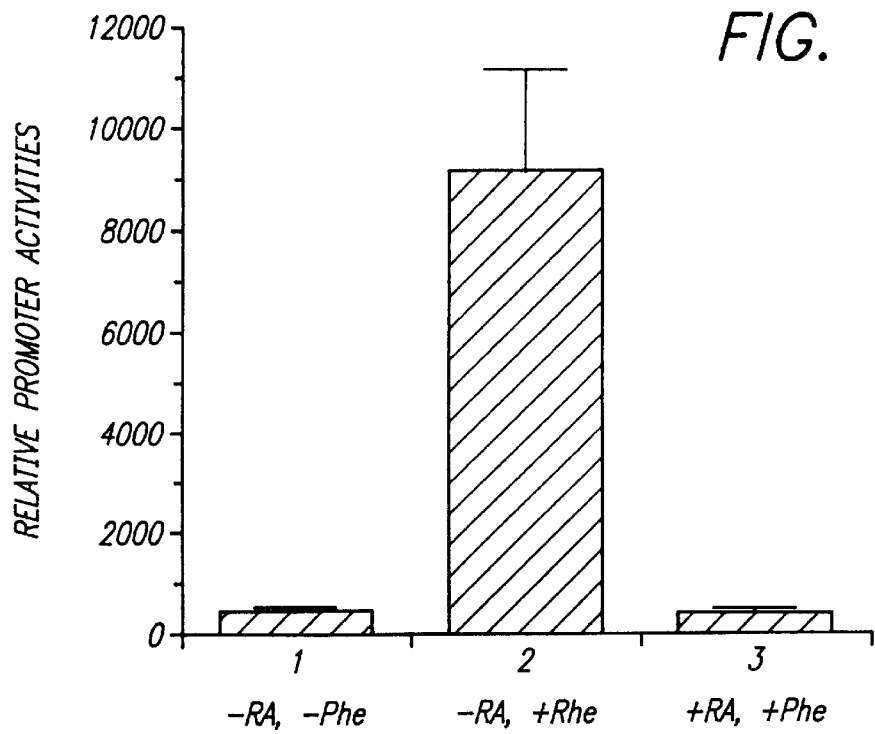
FIG. 1A is a graph showing the effect of Phe and RA on induction of gene expression in cells transfected with an ANF promoter-luciferase fusion gene construct. Transfected cells were cultured in maintenance medium (1: −RA−Phe), $2\times10^{-6}$ M Phe (2: −RA+Phe), or $1\times10^{-6}$ M RA+$2\times10^{-6}$ M Phe (3: +RA+Phe). Bars represent the effects of these agents relative to unstimulated cells. The luciferase activities were normalized by β-gal activities through co-transfection with a CMV-β-gal plasmid.

Utilizing an in vitro system of ventricular muscle cell hypertrophy, a role for retinoic acid compounds in suppressing the activation of the hypertrophic response by two well-defined hormonal stimuli, α-adrenergic agonists and endothelin-1, is demonstrated herein. The present invention demonstrates that hypertrophy suppressor pathways exist within cardiac muscle cells, and that retinoic acid compounds can activate these pathways. Thus, the invention provides a useful method for the treatment and prevention of ventricular muscle cell hypertrophy and for identifying compounds which activate hypertrophy suppressor pathways.

Before the methods of the invention are described, it is to be understood that this invention is not limited to the particular methods described. The terminology used herein is for the purpose of describing particular embodiments only, and is not intended to be limiting since the scope of the present invention will be limited only by the appended claims.

As used in this specification and the appended claims, the singular forms "a", "an", and "the" include plural references unless the context clearly dictates otherwise. Thus, for example, references to "retinoid acid" or "a retinoic acid compound" include mixtures of such retinoic acids, retinoids, and/or retinoic acid-like compounds, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference for the purpose of disclosing and describing the material for which the reference was cited in connection with.

Definitions

"Ventricular muscle cell hypertrophy" is a condition characterized by an increase in the size of individual ventricular muscle cells, the increase in cell size being sufficient to result in a clinical diagnosis of the patient or sufficient as to allow the cells to be determined as larger (e.g., 2-fold or more larger than non-hypertrophic cells). It may be accompanied by accumulation of contractile proteins within the individual cardiac cells and activation of embryonic gene expression.

In vitro and in vivo methods for determining the presence of ventricular muscle cell hypertrophy are known. In vitro assays for ventricular muscle cell hypertrophy include those methods described herein, e.g., increased cell size and increased expression on atrial natriuretic factor (ANF). Changes in cell size are used in a scoring system to determine the extent of hypertrophy. These changes can be viewed with an inverted phase microscope, and the degree of hypertrophy scored with an arbitrary scale of 7 to 0, with 7 being fully hypertrophied cells, and 3 being non-stimulated cells. The 3 and 7 states may be seen in Simpson et al., (1982) Circulation Res. 51:787–801, FIGS. 2, A and B, respectively. The correlation between hypertrophy score and cell surface area ($\mu m^2$) has been determined to be linear (correlation coefficient=0.99) (Dr. Kathleen L. King, Genentech, Calif.). In phenylephrine-induced hypertrophy, non-exposed (normal) cells have a hypertrophy score of 3 and a surface area/cell of 581 $\mu m_2$ and fully hypertrophied cells have a hypertrophy score of 7 and a surface area/cell of 1811 $\mu m^2$, or approximately 200% of normal. Cells with a hypertrophy score of 4 have a surface area/cell of 771 $\mu m^2$, or approximately 30% greater size than non-exposed cells; cells with a hypertrophy score of 5 have a surface area/cell of 1109 $\mu m^2$, or approximately 90% greater size than non-exposed cells; and cells with a hypertrophy score of 6 have a surface area/cell of 1366 $\mu m^2$, or approximately 135% greater size than non-exposed cells. The presence of ventricular muscle cell hypertrophy preferably includes cells exhibiting an increased size of about 15% (hypertrophy score 3.5) or more. Inducers of hypertrophy vary in their ability to induce a maximal hypertrophic response as scored by the above-described assay. For example, the maximal increase in cell size induced by endothelin is approximately a hypertrophy score of 5.

"Suppression" of ventricular muscle cell hypertrophy means a reduction in one of the parameters indicating hypertrophy relative to the hypertrophic condition, or a prevention of an increase in one of the parameters indicating hypertrophy relative to the normal condition. For example, suppression of ventricular muscle cell hypertrophy can be measured as a reduction in cell size relative to the hypertrophic condition. Suppression of ventricular muscle cell hypertrophy means a decrease of cell size of 10% or greater relative to that observed in the hypertrophic condition. More preferably, suppression of hypertrophy means a decrease of cell size of 30% or greater; most preferably, suppression of hypertrophy means a decrease of cell size of 50% or more. Relative to the hypertrophy score assay when phenylephrine is used as the inducing agent, these decreases would correlate with hypertrophy scores of about 6.5 or less, 5.0–5.5, and 4.0–5.0, respectively. When a different agent is used as the inducing agent, suppression is measured relative to the maximum cell size (or hypertrophic score) measured in the presence of that inducer.

Prevention of ventricular muscle cell hypertrophy is determined by preventing an increase in cell size relative to normal cells, in the presence of a concentration of inducer sufficient to fully induce hypertrophy. For example, prevention of hypertrophy means a cell size increase less than 200% greater than non-induced cells in the presence of a maximally-stimulating concentration of inducer. More preferably, prevention of hypertrophy means a cell size increase less than 135% greater than non-induced cells; and most preferably, prevention means a cell size increase less than 90% greater than non-induced cells. Relative to the hypertrophy score assay when phenylephrine is used as the inducing agent, prevention of hypertrophy in the presence of a maximally-stimulating concentration of phenylephrine means a hypertrophic score of about 6.0–6.5, 5.0–5.5, and 4.0–4.5, respectively.

In vivo determination of hypertrophy include measurement of cardiovascular parameters such as blood pressure, heart rate, systemic vascular resistance, contractility, force of heart beat, concentric or dilated hypertrophy, left ventricular systolic pressure, left ventricular mean pressure, left ventricular end-diastolic pressure, cardiac output, stroke index, histological parameters, and ventricular size and wall thickness. Animal models available for determination of development and suppression of ventricular muscle cell hypertrophy in vivo include the pressure-overload mouse model, RV murine dysfunctional model, transgenic mouse model, and post-myocardial infarction rat model. Medical methods for assessing the presence, development, and suppression of ventricular muscle cell hypertrophy in human patients are known, and include, for example, measurements of diastolic and systolic parameters, estimates of ventricular mass, and pulmonary vein flows.

The term "retinoic acid" as used herein is intended to include compounds having the following structure,

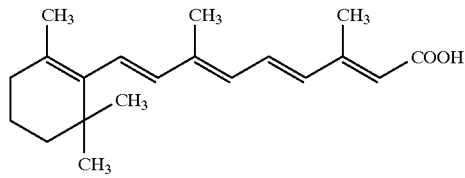

or pharmaceutical salts thereof, derivatives having a structure similar to that of retinoic acid, as well as biologically-equivalent derivatives thereof. Retinoic acid derivatives include natural and synthetic compounds having biochemically equivalent moieties bound to the carboxylic carbon atom. Typical salts are the alkalimetal and ammonium salts. Particularly preferred salts of the acid includ sodium, potassium, triethanloammonium and ammonium salts. Combinations of all the foregoing may be used in the method of the invention. Further, the terms "retinoic acid" are intended to include hydrogenated and nonhydrogenated isomers such as 9-cis-retinol, didehydroretinol, 13-cis-retinoic acid, 13-trans-retinoic acid, all-trans retinoic acid, and didehydroretinoic acid. The retinoic acid, derivatives, and retinoic acid-like molecules useful in the method of the invention are those characterized by the ability to bind retinoic acid receptors, thereby initiating the biological sequence of events leading to suppression of ventricular muscle cell hypertrophy. The derivatives may have such a structure when administered or may be converted to such a structure after administration, i.e., includes pro-drugs.

Retinoids are important therapeutic agents in the treatment of cancer and proliferative diseases of the skin (Jong et al. (1993) J. Med. Chem. 36:2605–2613). Retinoic acid (RA) and its synthetic analogs (retinoids) effect a wide array of biological processes by activating two distinct classes of nuclear receptor proteins, the retinoic acid receptors (RARs) (Giguere et al. (1990) Mol. Cell. Biol. 10:2335–2340) and the retinoid X receptors (RXRs) (Mangelsdorf et al. (1992) Genes Dev. 6:329–344). These retinoid receptors belong to the steroid/thyroid hormone receptor superfamily (Evans (1988) Science 240:889–895), and each class has three receptor subtypes, RAR-α, RAR-β, and RAR-γ, and RXR-α, RXR-β, and RXR-γ. A functional receptor, wherein functionality is defined in terms of the ability to activate DNA transcription, is a diner, either a homodimer (RXR/RXR) or a heterodimer (RAR/RXR). Retinoic acid derivatives and retinoic acid-like compounds that are capable of binding RXR, RAR, or both, include 9-cis-retinoic acid, all-trans retinoic acid, (E)-4-[2-(5,5,8,8-tetramethyl-5,6,7,8-tetrahydro-2-naphthalenyl)-1-propenyl]benzoic acid (TTNPB), and (E)-4-[2-(3,5,5,8,8-pentamethyl-5,6,7,8-tetrahydro-2-naphthalenyl)-1-propenyl]benzoic acid (3-methyl-TTNPB), and LG64. Evidence suggests a central role for RXR in regulating several distinct hormonal response pathways. One function of RXR is to act as an auxiliary receptor for several nuclear receptors, including the RARs, thyroid hormone receptors and vitamin D receptor. Heterodimers of RXR with these receptors form in solution (Zhang et al. (1992a) Nature 355:441–446) and bind selectively with high affinity to specific hormone response elements (Hermann et al. (1992) Mol. Endocrinol. 6:1153–1162). RXRs also function independently as homodimers (Zhang et al. (1992b) Nature 358:587–591) which form in the presence of the 9-cis isomer of all-trans RA, and have different response element specificities than the RAR:RXR heterodimers (Hermann et al. (1992) supra; Zhang et al. (1992b) supra). In contrast, RARs bind both ligands with high affinity (Heyman et al. (1992) Cell 68:397–406). The use of molecules which are biologically equivalent, e.g., able to bind retinoic acid receptors to suppress ventricular muscle cell hypertrophy, is included in the method of the invention.

By the term "effective amount" or "therapeutically effective amount" of retinoic acid is meant an amount of a retinoic acid compound, retinoic acid derivative and/or a retinoic acid-like compound sufficient to obtain the desired physiological effect, e.g., suppression of ventricular muscle cell hypertrophy. An effective amount of retinoic acid is determined by the caregiver in each case on the basis of factors normally considered by one skilled in the art to determine appropriate dosages, including the age, sex, and weight of the subject to be treated, the condition being treated, and the severity of the medical condition being treated.

The terms "treatment" "treating" and the like are used herein to generally mean obtaining a desired pharmacologic and/or physiologic effect. The effect may by prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease. The invention is directed to treating patients with or at risk for development of ventricular muscle cell hypertrophy and related conditions mediated by ventricular muscle cell hypertrophy, e.g., heart failure. More specifically, "treatment " is intended to mean providing a therapeutically detectable and beneficial effect on a patient suffering from ventricular muscle cell hypertrophy or a condition mediated by ventricular muscle cell hypertrophy.

Still more specifically, "treatment" shall mean preventing, alleviating, and/or inhibiting (1) ventricular muscle cell hypertrophy mediated through $\alpha_1$-adrenergic agonists, (2) ventricular muscle cell hypertrophy mediated through endothelin, (3) ventricular muscle cell hypertrophy mediated through drugs known to have the adverse effect of promoting cardiac hypertrophy, (4) a medical condition, e.g., heart failure, mediated by ventricular muscle cell hypertrophy induced by $\alpha_1$-adrenergic agonists, endothelin, and/or drugs which promote cardiac hypertrophy, and (5) ventricular muscle cell hypertrophy initiated by cardiac injury, such as viral myocarditis, long-standing hypertension, cardiomyopathy due to pathological stimuli, and post-myocardial infarction.

By the term "$\alpha_1$-adrenergic-mediated ventricular muscle cell hypertrophy" is meant ventricular muscle cell hypertrophy which results from activation of $\alpha_1$-adrenergic receptors by $\alpha_1$-adrenergic agonists. $\alpha_1$-adrenergic agonists include natural agonists, such as epinephrine, and synthetic agonists, such as phenylephrine or methoxamine.

By the term "endothelin" is meant a peptide compound of the endothelin family, including, endothelin-1, endothelin-2, and endothelin-3, which induces ventricular muscle cell hypertrophy.

By the term "heart failure" is meant an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, and myocarditis. The heart failure can be caused by any number of factors, including ischemic, congenital, rheumatic, or idiopathic forms. Chronic cardiac hypertrophy is a significantly diseased state which is a precursor to congestive heart failure and cardiac arrest.

"Treatment" refers to both therapeutic treatment and prophylactic or preventative measures, wherein the object is to prevent or slow down (lessen) hypertrophy. Those in need of treatment include those already with the disorder as well as those prone to have the disorder or those in which the disorder is to be prevented. The hypertrophy may be from any cause which is responsive to retinoic acid, including congenital, viral, idiopathic, cardiotrophic, or myotrophic causes, or as a result of ischemia or ischemic insults such as myocardial infarction. Typically, the treatment is performed to stop or slow the progression of hypertrophy, especially after heart damage, such as from ischemia, has occurred. Preferably, for treatment of myocardial infarctions, the agent (s) is given immediately after the myocardial infarction, to prevent or lessen hypertrophy.

The terms "synergistic", "synergistic effect" and like are used herein to describe improved treatment effects obtained by combining one or more therapeutic agents with one or more retinoic acid compounds. Although a synergistic effect in some field is meant an effect which is more than additive (e.g., 1+1=3), in the field of medical therapy an additive (1+1=2) or less than additive (1+1=1.6) effect may be synergistic. For example, if each of two drugs were to inhibit the development of ventricular muscle cell hypertrophy by 50% if given individually, it would not be expected that the two drugs would be combined to completely stop the development of ventricular muscle cell hypertrophy. In many instances, due to unacceptable side effects, the two drugs cannot be administered together. In other instances, the drugs counteract each other and slow the development of ventricular muscle cell hypertrophy by less than 50% when administered together. Thus, a synergistic effect is said to be obtained if the two drugs slow the development of ventricular muscle cell hypertrophy by more than 50% while not causing an unacceptable increase in adverse side effects.

"Chronic" administration refers to administration of a retinoic acid compound in a continuous mode as opposed to an acute mode, so as to maintain the initial anti-hypertrophic effect for an extended period of time.

Retinoic Acid Suppression of Ventricular Muscle Cell Hypertrophy.

To evaluate the effect of a retinoic acid compound on the hypertrophic response, an in vitro model system was used in which defined agonists can activate several independent features of ventricular muscle cell hypertrophy (Example 1). Treatment with the $\alpha_1$-adrenergic agonist phenylephrine (Phe) results in an increase in ventricular muscle cell size and assembly of MLC-2v protein into organized sarcomeric units relative to control cells. Phe-stimulated increase in cell size is largely prevented by RA, while myofibrillar organization appears to be intact, and the cells continue to exhibit spontaneous contractility (data not shown). Treatment with RA alone had little effect on the ventricular muscle cell phenotype, indicating that the effect of RA was not secondary to a toxic cellular effect. Features of hypertrophy are also induced by the addition of serum. However, the addition of RA had little effect on the serum-treated cells, suggesting that RA has a selective specificity for inhibition of the $\alpha_1$-adrenergic pathway. A direct measurement of cell size (Table 1) indicates that Phe or serum increase cell size approximately 3-fold, while RA treatment specifically suppresses the Phe induction to near background levels. Taken together, these data indicate that pharmacological concentrations of retinoic acid selectively suppress the hypertrophic response following $\alpha_1$-adrenergic stimulation.

To examine the effects of RA on the induction of atrial natriuretic factor (ANF), total RNA was isolated from ventricular muscle cells cultured in maintenance media alone, or maintenance media supplemented with Phe, RA, or both agents (Example 2). Phe induces ANF mRNA expression by approximately 6-fold relative to control (Table 2). In contrast, combined treatment with both RA and Phe results in levels of ANF mRNA comparable to unstimulated cells, consistent with an effect of RA on inhibiting the hypertrophic phenotype. RA suppression of Phe induction of the ANF mRNA was dose-dependent (Table 3) with a 50% suppression seen with a RA concentration less than $10^{-8}$ M, which is within physiological levels and comparable to the dose response profile for transcriptional activation mediated by retinoid receptors (Gigvere et al. (1987) Nature 330:634–629).

The effects of Phe and RA treatment on the expression of troponin I (TnI) mRNA and myosin light chain 2v (MLC-2v) mRNA was determined, both constitutively expressed cardiac muscle genes. As displayed in Table 2, RA had no detectable effect on inhibiting the expression of the TnI or MLC-2v gene during Phe stimulation. Similar results were obtained at the protein level in studies employing dual immunofluorescence with MLC-2v and ANF antibodies (data not shown). Taken together, these results indicate that RA treatment selectively inhibits the expression of a genetic marker of the ventricular muscle cell hypertrophic response, ANF, at both the protein and RNA levels.

Endothelin, a naturally occurring peptide derived from endothelial cells, is a potent constrictor of vascular smooth muscle (Yanagisawa et al. (1989) Trends Pharmacol. Sci. 10:374–378). To date, three endothelin-related peptides have been identified, endothelin-1, -2, and -3 (Inoue et al. (1989) Proc. Natl. Acad. Sci. U.S.A. 86:2863–2867). Endothelin-1 is a 21 amino acid peptide which is a potent venous and arterial vasoconstrictor. The mature biologically active peptide is a proteolytic product of the 38–39 amino acid molecule "big endothelin" (Yanagisawa et al. (1989) supra). Endothelin has been shown to induce protein tyrosine phosphorylation in aortic smooth muscle cells, mesangial cells, and osteoblast-like cells (Battistini et al. (1993) Peptides 14:385–399), but in neonatal rat ventricular muscle cells in culture, endothelin, like the $\alpha$-adrenergic agents, stimulates phosphoinositide hydrolysis and the accumulation of diacylglycerol (Shubeita et al. (1990) supra). Endothelin is present in vivo in both atrial and ventricular myocardium in healthy and failing hearts and enhances myocardial inotropic activity, vascular smooth muscle proliferation and coronary vasoconstriction (Wei et al. (1994) Circulation 89:1580–1586). Endothelin stimulates multiple cell-signalling pathways in cultured adult cardiac myocytes (Hilal-Dandan et al. (1994) Mol. Pharm. 45:1183–1190; Jones et al. (1992) Am. J. Physiol. 263:H1447–H1454). Several investigators have shown that endothelin-1 induces hypertrophy of ventricular muscle cells in vitro (Shubeita et al. (1990) supra; Ito et al. (1991) Circ. Res. 69:209–215; Suzuki et al. (1991) J. Cardiovasc. Pharmacol. 17 Suppl. 7:S182–S186. See, also U.S. Pat. No. 5,344,644. Endothelin receptor antagonists include compounds such as BQ-123 (Ihara et al. (1992) Life Science 50:247–0250; Webb et al. (1992) Biochem. Biophys. Res. Commun. 185:887–892). BQ-123 is a cyclic pentapeptide that is a potent and specific blocker of endothelin A receptors, able to block the hypertrophic activity induced by endothelin-1, but not that induced by phenylephrine.

Figure 1B:
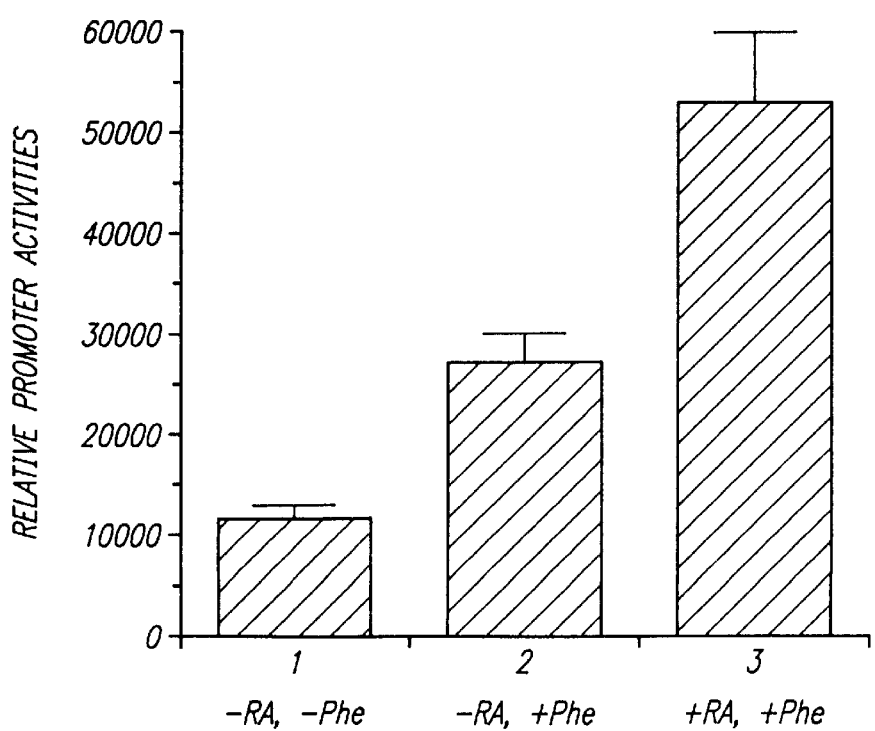
FIG. 1B is a graph showing the effect of Phe and RA on induction of gene expression in cells transfected with an Rous sarcoma virus (RSV) promoter-luciferase fusion gene construct. Transfected cells were cultured in maintenance medium (1: −RA−Phe), $2\times10^{-6}$ M Phe (2: −RA+Phe), or $1\times10^{-6}$ M RA+$2\times10^{-6}$ M Phe (3: +RA+Phe). Bars represent the effects of these agents relative to unstimulated cells. The luciferase activities were normalized by β-gal activities through co-transfection with a CMV-β-gal plasmid.
Figure 1C:
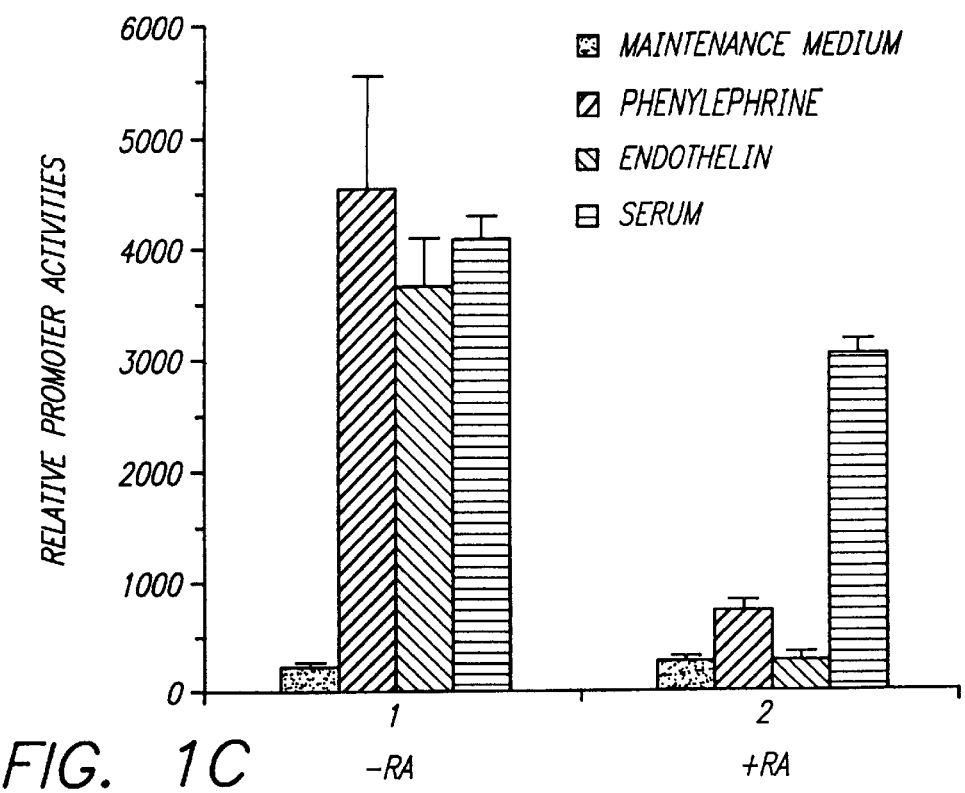
FIG. 1C is a graph showing the induction of luciferase expression in cells transfected with a ANF promoter-luciferase fusion gene construct. Transfected cells were cultured in maintenance medium, $2\times10^{-6}$ M Phe, $1\times10^{-8}$ M endothelin, or 10% FBS, with or without $1\times10^{-6}$ M RA. Bars represent the effects of these agents relative to unstimulated cells. The luciferase activities were normalized by β-gal activities through co-transfection a CMV-β-gal plasmid.

A series of studies have identified cis sequences within the ANF promoter region which can confer $\alpha$-adrenergic inducibility to a luciferase reporter gene in transient transfection assays (Knowlton et al. (1991) supra; Argentin et al. (1991) J. Biol. Chem. 266:23315–23322; Grepin et al. (1994) Mol. Cell. Biol. 14:3115–3129). When introduced into ventricular muscle cells cultured in maintenance media, Phe, endothelin-1, and serum induces a 15- to 20-fold induction of a 3003 ANF promoter-luciferase fusion gene (Example 3). The induction by Phe or endothelin-1 is suppressed to basal levels by the addition of RA (FIGS. 1A and 1C). As a control, the expression of the Rous sarcoma virus (RSV) LTR promoter was not inhibited by RA, and was in fact stimulated slightly by both Phe and RA (FIG. 1B), indicating the specificity of the suppressing activity of RA for the ANF promoter.

The induction of the ANF promoter caused by the peptide growth factor endothelin I (FIG. 1C), acts through a specific cell-surface receptor coupled to signaling pathways which intersect with $\alpha$-adrenergic signal transduction, and is thus suppressible by RA. In contrast, RA had little effect on suppressing the induction of the ANF luciferase reporter gene following serum stimulation, consistent with the results described above of the RA effect on serum stimulation of cell size (Example 1). The inability of RA to suppress serum inducibility of the ANF-luciferase reporter gene suggests that retinoid signaling pathways do not directly inhibit ANF promoter activity, but rather may induce a functional blockade at a step in $\alpha$-adrenergic and endothelin-1 signal transduction pathways of ventricular muscle cell hypertrophy.

Figure 2A:
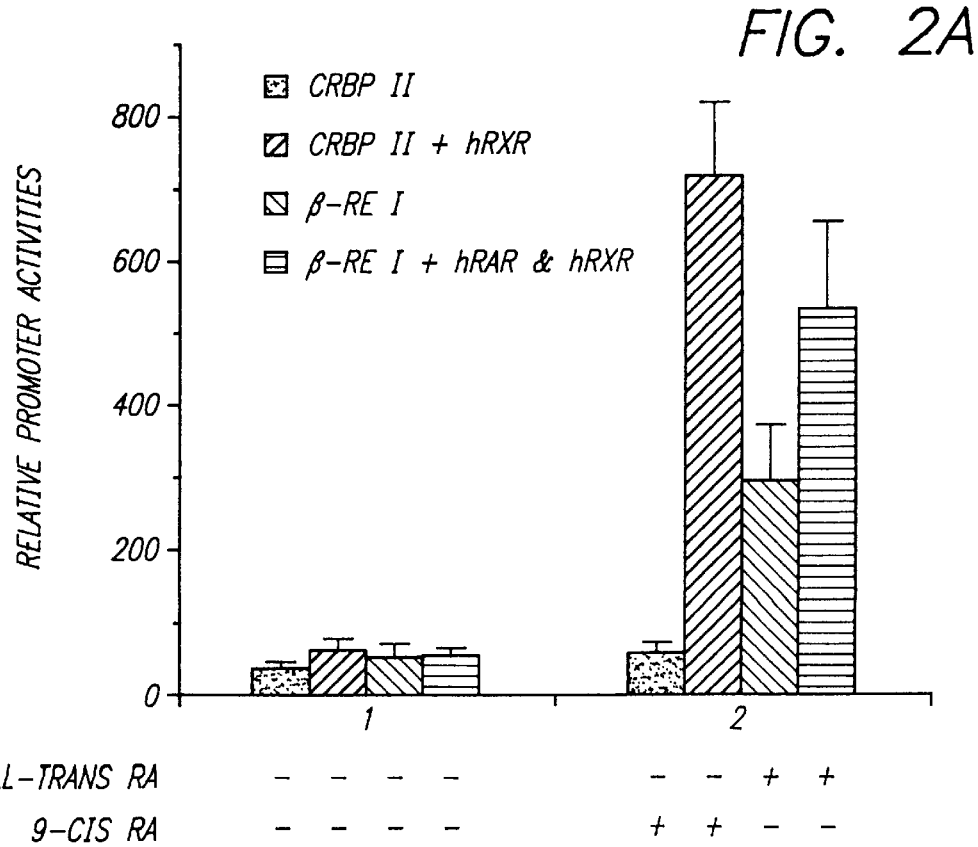
FIG. 2A is a graph showing activation of RA receptors in cultured ventricular cells. Reporter plasmids containing CRBP II-luciferase or β-RE I-luciferase were transfected into ventricular muscle cells without or with co-transfected expression plasmids containing human RXRα or RARα cDNA driven by a CMV promoter. 9-cis RA or all-trans RA were separately added to the cultures to activate CRBP II or β-RE I promoters. Bars represent the effects of ligands on the promoter activities relative to reporter gene activity in the absence of ligand.

To assay the activity of retinoic acid receptors in cultured ventricular muscle cells, response elements specific for activation by the RXR homodimer (CRBP II) (Mangelsdorf et al. (1991) supra) or by the RAR/RXR heterodimer (β-RE I) (Sucov et al. (1990) supra) were cloned into an enhancer-dependent heterologous reporter context and introduced by transfection (Example 4). As shown in FIG. 2A, the CRBP II reporter construct was not activated by endogenous receptors in the presence of 9cRA, yet was up-regulated when co-transfected with an RXR-expression construct. In contrast, the β-RE I heterodimer reporter gene is functional in the presence of ligand using the endogenous complement of receptors, and this activity can be further increased by co-transfection of receptor expression constructs. These results demonstrate that cultured neonatal ventricular cardiomyocytes express a functional retinoic acid receptor complex of both RARs and RXRs, which can transactivate through at least one of the known RA response pathways.

Figure 2B:
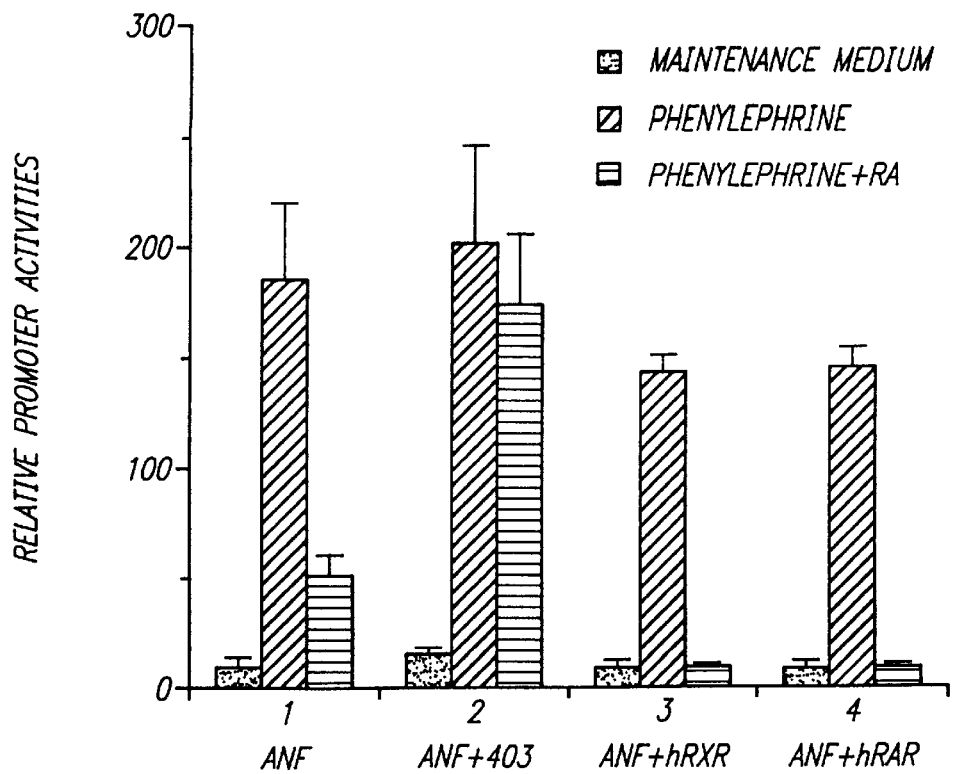
FIG. 2B is a graph showing the effect of Phe+RA on activation of a reporter construct containing the ANF promoter alone; the ANF promoter with a dominant negative reporter construct (CMV-hRAR403), the wild-type receptor construct (CMV-hRXR), or the wild-type receptor construct CMV-hRAR in ventricular muscle cells cultured in maintenance medium, or $2\times10^{-6}$ M Phe with or without $1\times10^{-7}$ M all-trans RA. The percent of Phe induction is expressed as the ratio of fold increase in the reporter gene by Phe in the presence of RA to the fold increase in the reporter gene observed following Phe stimulation in the absence of RA.

Recently, a truncation deletion mutant of the RARα receptor has been described which functions as a transdominant negative, hRXRα403, able to block normal retinoic acid induced transcriptional transactivation through both the RXR/RAR heterodimer and the RXR homodimer pathways (Damm et al. (1993) Proc. Natl. Acad. Sci. U.S.A. 90:2989–2993). The effects of expression of this mutant receptor on induction of the ANF promoter was studied (Example 5) and the results are shown in FIG. 2B. RA was ineffective in suppressing Phe induction of gene expression in the presence of the dominant negative mutant receptor. Co-transfection of hRXRα403 with the ANF-luciferase reporter gene in the presence of RA retains 83% of the Phe induction of ANF promoter activity, in comparison with only 23% of the Phe inducible activity observed in the absence of hRXRα403. In contrast, forced expression of either RAR or RXR results in an enhancement of the suppressing activity of RA. These results demonstrate that the suppression of Phe-induced ANF expression by RA is mediated through the endogenous RA receptors.

Figure 3A:
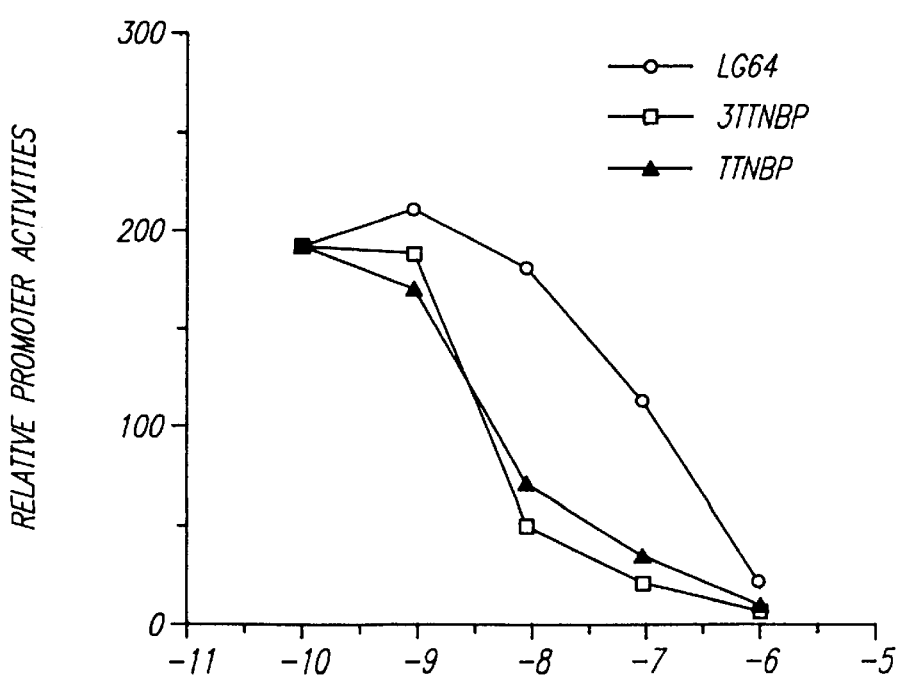
FIG. 3A is a graph of induction of luciferase expression in cells transfected with the ANF-luciferase reporter gene construct and activated by $2\times10^{-6}$ M Phe with a series of concentrations of three agonists; LG64, (E)-4-[2-(5,5,8,8-tetramethyl-5,6,7,8-tetrahydro-2-naphthalenyl)-1-propenyl] benzoic acid (TTNPB), and (E)-4-[2-(3,5,5,8,8-pentamethyl-5,6,7,8-tetrahydro-2-naphthalenyl)-1-propenyl]benzoic acid (3-methyl-TTNBP). Curves represent the relative luciferase activities normalized by the β-gal activities.

In cultured cells, atRA and 9cRA are reversibly isomerized; consequently, in transactivation assays, treatment with either compound potentially activates both the RXR/RAR heterodimer and RXR homodimer pathways. Recent advances have led to the development of stable synthetic retinoids which are selective agonists for either the RARs or the RXRs and which are not subject to metabolic conversion. Among such agonists, the compound (E)-4-[2-(5,5,8,8-tetramethyl-5,6,7,8-tetrahydro-2-naphthalenyl)-1-propenyl]benzoic acid (TTNPB) is selective for the RARs, the compound (E)-4-[2-(3,5,5,8,8-pentamethyl-5,6,7,8-tetrahydro-2-naphthalenyl)-1-propenyl]benzoic acid (3-methyl-TTNPB) is a pan-agonist for both the RARs and the RXRs, and the compound LG64 is selective for the RXRs, although there is some degree of crossover at higher concentrations for both TTNPB and LG64. The ability of these compounds to block Phe induced expression of the ANF promoter was tested (Example 5), and the results are shown in FIG. 3A. TTNPB and 3-methyl-TTNPB are equivalent in their potency to block induction of the ANF promoter, whereas the RXR-selective compound LG64 is approximately 40-fold less potent in this assay. Similarly, the hypertrophic increase in cell size induced by Phe was prevented by TTNPB and not by LG64 (data not shown). This indicates that ligand activation of the RAR is the essential component in blocking the α-adrenergic induction of hypertrophy, as monitored both by cell size and by the expression of the ANF promoter.

Figure 3B:
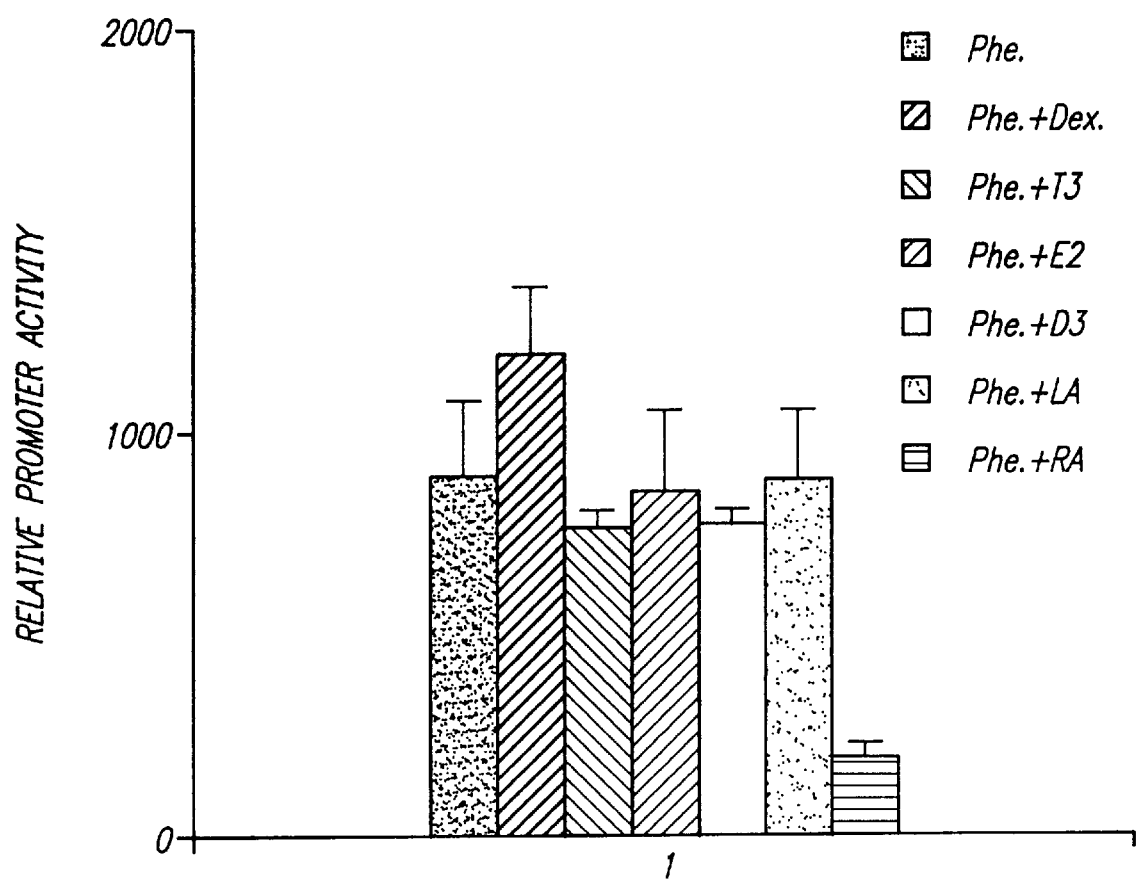
FIG. 3B is a graph of the induction of luciferase activity in cells transfected with the ANF-luciferase reporter gene construct and exposed to $2\times10^{-7}$ M Phe and one of the following: $1\times10^{-7}$ M dexamethasone (Dex), $1\times10^{-7}$ M thyroid hormone (T3), $1\times10^{-7}$ M estrogen (E2), $1\times10^{-7}$ M vitamin D (D3), $1\times10^{-7}$ M linoleic acid (LA), and $1\times10^{-7}$ M retinoic acid (RA).

Retinoic acid receptors belong to the larger family of nuclear receptors which also mediate the effects of steroid and thyroid hormones and vitamin D. The possibility that these other hormonal signaling pathways impact PE-induced hypertrophy was determined (Example 7). Cultured ventricular muscle cells were transfected with the ANF promoter reporter construct and co-cultured with PE and additional hormones. As shown in FIG. 3B, only treatment with RA prevented the induction of the ANF promoter. Treatment with thyroid hormone, estrogen, and vitamin D were inactive in this assay, and dexamethasone (a synthetic glucocorticoid) actually increased ANF expression. This latter observation has been previously reported and occurs through a non-hypertrophic pathway without an increase in cell size. These results show that the α-adrenergic induction of hypertrophy is specifically blocked by RA, and not by other hormones.

The specific signal transduction pathways which ultimately result in induction of ventricular muscle cell hypertrophy are currently unknown. Since retinoic acid is selective in blocking both the α-adrenergic and endothelin-1 pathways of in vitro ventricular muscle cell hypertrophy, but is ineffective on the serum-induced hypertrophic response, it is clear that the ventricular muscle cell is able to modulate its growth response through multiple parallel pathways. Furthermore, while RA blocks the increase in cell size and the induction of ANF expression following α-adrenergic stimulation, RA does not prevent myofibrillar reorganization or the induction of contractility. This suggests that multiple effector pathways emerge from the α-adrenergic receptor, as has in fact been previously documented (Thorburn et al. (1993) supra; LaMorte et al. (1994) supra), and that the inhibitory effects of RA are manifest at an intermediate point in a portion of the downstream α-adrenergic pathways, but does not block all of the α-adrenergic receptor dependent signals.

In addition to directly regulating gene expression, an additional pathway in which retinoids have biological consequences has been described, in which ligand-activated receptors block the activity of the transcription factor AP-1 (Schule et al. (1991) Proc. Natl. Acad. Sci. U.S.A. 88:6092–6096; Salbert et al. (1993) Molec. Endocrinol. 7:1347–1356). This process, termed cross-coupling, does not require DNA binding of the receptor, but rather appears to be a protein-protein interaction between a retinoid receptor and c-jun, and likely additional proteins as well. AP-1 activity is induced in many signal transduction pathways, and the ANF promoter has sequences which are similar to AP-1 binding sites (Knowlton et al. (1991) supra). However, cross-coupling is probably not sufficient to explain at a mechanistic level the suppression of hypertrophy caused by retinoic acid. While multiple hormone receptors can engage in cross-coupling, including the glucocorticoid receptor, the results presented herein indicate that suppression of hypertrophy is not seen following the addition of glucocorticoids (data not shown). Consequently, the most likely explanation for the observed results is that retinoic acid induces the expression of a select subset of cardiac genes through the RXR/RAR heterodimer, and that these induced gene products are able to block specific aspects of downstream signal transduction stimulated by the α-adrenergic and endothelin receptors, leading to suppression of the hypertrophic phenotype.

Retinoic acid has additional consequences on cardiomyocytes in addition to simply suppressing α-adrenergic receptor mediated hypertrophy. In neonatal cells, RA induces expression of MLC-2v, as shown herein, and has been previously reported to induce the adult form of α-myosin heavy chain (Rohrer et al. (1991) J. Biol. Chem.

266:8638–8646). During the hypertrophic response, ventricular muscle cells express embryonic markers, such as the ANF, skeletal α-actin and β-myosin heavy chain genes, and thereby exit from the mature, adult ventricular phenotype (for review see, Chien et al. (1991) FASEB J. 5:303–3046). The ability of retinoids to suppress the expression of atrial and embryonic markers during hypertrophy in the post-natal state, coupled with their ability to promote the ventricular phenotype in the embryonic state, raises the possibility that retinoid dependent pathways function in the adult myocardium to actively maintain the ventricular phenotype. In this manner, the activation of a hypertrophic response may be related, in part, to the relief of retinoid suppression.

The recent demonstration that ras is sufficient to activate hypertrophy in both in vitro and in vivo model systems of hypertrophy is consistent with the findings herein that retinoic acid compounds suppress the hypertrophic response. In other cell types, retinoic acid compounds can inhibit ras dependent pathways for proliferation and differentiation (Cox et al. (1991) J. Cancer Res. Clin. Oncol. 117:102–108; Leder et al. (1990) Proc. Natl. Acad. Sci. U.S.A. 87:9178–9182). In addition, recent studies in RXRα gene targeted mice have documented a requirement for vitamin A for normal maturation of ventricular muscle cells during cardiogenesis (Sucov et al. (1994) Genes Dev. 8:1007–1018). RXRα−/−embryos display the persistent, aberrant expression of an atrial marker (MLC-2a) in the ventricular chamber, a phenotype that is closely associated with an embryonic form of heart failure (Dyson et al. (1995) Proc. Natl. Acad. Sci. U.S.A. (In Press)). The clear role of vitamin A-dependent pathways in promoting the ventricular phenotype in the embryonic heart is consistent with the findings herein that retinoic acid compounds are also important in maintaining the normal ventricular phenotype in the postnatal state, as well. Since hypertrophy is associated with the expression of atrial markers in the ventricular chamber (such as ANF), the ability of retinoic acid compounds to maintain a normal ventricular phenotype in the presence of defined hypertrophic stimuli demonstrates the role of retinoic acid compounds in the maintenance of the ventricular muscle phenotype in the postnatal state.

Therapeutic Use

The present invention provides methods for treating or preventing heart failure and ventricular muscle cell hypertrophy in a mammal by providing an effective amount of a retinoic acid compound. Preferably, the mammal is a human patient suffering from or at risk of developing heart failure.

The present invention is useful in preventing ventricular muscle cell hypertrophy in patients being treated with a drug which cause cardiac hypertrophy, e.g., fludrocortisone acetate. In the method of the invention, a retinoic acid compound can be given prior to, simultaneously with, or subsequent to a drug which causes cardiac hypertrophy.

In the therapeutic method of the invention, a retinoic acid compound is administered to a human patient chronically or acutely. Optionally, retinoic acid is administered chronically in combination with an effective amount of a compound that acts to suppress a different hypertrophy induction pathway than a retinoid. Additional optional components include a cardiotrophic inhibitor such as a CT-1 antagonist, an ACE inhibitor, such as captopril, and/or human growth hormone and/or IGF-I in the case of congestive heart failure, or with another anti-hypertrophic, myocardiotrophic factor, anti-arrhythmic, or inotropic factor in the case of other types of heart failure or cardiac disorder.

The present invention can be combined with current therapeutic approaches for treatment of heart failure, e.g., with ACE inhibitor treatment. ACE inhibitors are angiotensin-converting enzyme inhibiting drugs which prevent the conversion of angiotensin I to angiotensin II. The ACE inhibitors may be beneficial in congestive heart failure by reducing systemic vascular resistance and relieving circulatory congestion. ACE inhibitors include drugs designated by the trademarks Accupril® (quinapril), Altace® (ramipril), Capoten® (captopril), Lotensin® (benazepril), Monopril® (fosinopril), Prinivi® (lisinopril), Vasotec® (enalapril), and Zestril® (lisinopril).

The present invention can be combined with the administration of drug therapies for the treatment of heart diseases such as hypertension. For example, a retinoic acid compound can be administered with endothelin receptor antagonists, for example, an antibody to the endothelin receptor, and peptide or other small molecule antagonists; β-adrenoceptor antagonists such as carvedilol; $α_1$-adrenoceptor antagonists; anti-oxidants; compounds having multiple activities (e.g., β-blocker/α-blocker/anti-oxidant); carvedilol-like compounds or combinations of compounds providing multiple functions found in carvedilol; growth hormone, etc.

Retinoic acid receptors RAR (α, β and γ) and RXR (α, β and γ) function biologically to active DNA transcription in the forms of the RXR homodimer and RAR/RXR heterodimer. RXRα subtype may be an key target based on in vivo data observed with dominant, negative RXRα-mutant subtype expressed in transgenic mice. Pan-agonists, those that have specificity for both RAR and RXR, are preferred agonists since it is the heterodimer (RAR/RXR) that likely mediates the retinoid hypertrophy suppression effect. Less preferred are those that recognize only RAR. And least preferred are those that recognize only RXR. However, none of the known retinoid receptor agonists appear to have specificity solely for only one family; some cross-specificity can exist as evidence by the ability of LG64 (RXR specific) to suppress at high concentrations. Also preferred are those that are specific for a RAR subtype (α, β, or γ) that mediates suppression of ventricular muscle cell hypertrophy.

Retinoid agonists alone or in combination with other hypertrophy suppressor pathway agonists or with molecules that antagonize known hypertrophy induction pathways, are useful as drugs for in vivo treatment of mammals experiencing heart failure, so as to prevent or lessen hypertrophic effects.

Therapeutic formulations of agonist(s) for treating heart disorders are prepared for storage by mixing the agonist(s) having the desired degree of purity with optional physiologically acceptable carriers, excipients, or stabilizers (*Remington's Pharmaceutical Sciences*, 16th edition, Oslo, A., Ed., 1980), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or non-ionic surfactants such as Tween, Pluronics, or polyethylene glycol (PEG). The antagonist(s) are also suitably linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. The amount of carrier used in a formulation may range from about 1 to 99%, preferably from about 80 to 99%, optimally between 90 and 99% by weight.

The agonist(s) to be used for in vivo administration must be sterile. This is readily accomplished by methods known in the art, for example, by filtration through sterile filtration membranes, prior to or following lyophilization and reconstitution. The agonist(s) ordinarily will be stored in lyophilized form or in solution.

Therapeutic agonist compositions generally are placed into a container having a sterile access port, for example, an intravenous solution bag or vial having a stopper pierceable by a hypodermic injection needle.

The agonist(s) administration is in a chronic fashion using, for example, one of the following routes: injection or infusion by intravenous, intraperitoneal, intracerebral, intramuscular, intraocular, intraarterial, or intralesional routes, orally or using sustained-release systems as noted below. Agonist(s) is administered continuously by infusion or by periodic bolus injection if the clearance rate is sufficiently slow, or by administration into the blood stream or lymph. The preferred administration mode is targeted to the heart, so as to direct the molecule to the source and minimize side effects of the agonists.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al. (1981) J. Biomed. Mater. Res. 15:167–277 and Langer (1982) Chem. Tech. 12:98–105, or poly(vinyl alcohol)), polylactides (U.S. Pat. No. 3,773,919, EP 58,481), copolymers of L-glutamic acid and gamma ethyl-L-glutamate (Sidman et al. (1983) Biopolymers 22:547–556), non-degradable ethylene-vinyl acetate (Langer et al. (1981) supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133, 988).

The agonist(s) also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

While polymers such as ethylene-vinyl acetate and lactic acid-glycolic acid enable release of molecules for over 100 days, certain hydrogels release molecules for shorter time periods. When encapsulated molecules remain in the body for a long time, they may denature or aggregate as a result of exposure to moisture at 37° C., resulting in a loss of biological activity and possible changes in immunogenicity. Rational strategies can be devised for stabilization depending on the mechanism involved, e.g., using appropriate additives, and developing specific polymer matrix compositions.

Sustained-release agonist(s) compositions also include liposomally entrapped agonist(s). Liposomes containing agonist(s) are prepared by methods known per se: DE 3,218,121; Epstein et al. (1985) Proc. Natl. Acad. Sci. U.S.A. 82:3688–3692; Hwang et al. (1980) Proc. Natl. Acad. Sci. U.S.A. 77:4030–4034; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol % cholesterol, the selected proportion being adjusted for the optimal agonist therapy. A specific example of a suitable sustained-release formulation is in EP 647,449.

An effective amount of agonist(s) to be employed therapeutically will depend, for example, upon the therapeutic objectives, the route of administration, and the condition of the patient. Accordingly, it will be necessary for the clinician to titer the dosage and modify the route of administration as required to obtain the optimal therapeutic effect. A typical daily dosage of a retinoic acid compound used alone might range from about 1 μg/kg to up to 100 mg/kg of patient body weight or more per day, depending on the factors mentioned above, preferably about 10 μg/kg/day to 50 mg/kg/day.

If the two agonists are administered together, they need not be administered by the same route, nor in the same formulation. However, they can be combined into one formulation as desired. Both agonists can be administered to the patient, each in effective amounts, or each in amounts that are sub-optimal but when combined are effective. Preferably such amounts are about 10 μg/kg/day to 50 mg/kg/day of each. In one embodiment, the administration of both agonists is by injection using, e.g., intravenous or subcutaneous means, depending on the type of agonist employed. Typically, the clinician will administer the agonist(s) until a dosage is reached that achieves the desired effect for treatment of the heart dysfunction. For example, the amount would be one which decreases ventricular muscle cell hypertrophy, increases ventricular contractility, and decreases peripheral vascular resistance or ameliorates or treats conditions of similar importance in congestive heart failure patients, thus obtaining the result desired in the continuum of equilibria between growing and shrinking of cardiac muscle tissue. The progress of this therapy is easily monitored by conventional assays.

The two types of agonists, if used together, may be formulated together in an appropriate carrier vehicle to form a pharmaceutical composition that preferably does not contain cells. In one embodiment, the buffer used for formulation will depend on whether the composition will be employed immediately upon mixing or stored for later use, since long-term storage may bring into issue stability such as solubility and aggregation that can be addressed by altering the pH. The final preparation may be a stable liquid or lyophilized solid.

The agonist(s) optionally is combined with or administered in concert with other agents for treating congestive heart failure, including ACE inhibitors, CT-1 inhibitors, human growth hormone, and/or IGF-I.

The effective amounts of such agents, if employed, will be at the clinician's discretion. Dosage administration and adjustment are determined by methods known to those skilled in the art to achieve the best management of congestive heart failure and ideally takes into account use of diuretics or digitalis, and conditions such as hypotension and renal impairment. The dose will additionally depend on such factors as the type of drug used and the specific patient being treated. Typically the amount employed will be the same dose as that used if the drug were to be administered without agonist; however, lower doses may be employed depending on such factors as the presence of side-effects, the condition being treated, the type of patient, and the type of agonist and drug, provided the total amount of agents provides an effective dose for the condition being treated.

Thus, for example, in the case of ACE inhibitors, a test dose of enalapril is 5 mg, which is then increased up to 10–20 mg per day, once a day, as the patient tolerates it. As another example, captopril is initially administered orally to human patients in a test dose of 6.25 mg and the dose is then escalated, as the patient tolerates it, to 25 mg twice per day (BID) or three times per day (TID) and may be titrated to 50 mg BID or TID. Tolerance level is estimated by determining whether decrease in blood pressure is accompanied by signs of hypotension. If indicated, the dose may be increased up to 100 mg BID or TID. Captopril is produced for administration as the active ingredient, in combination with hydrochlorothiazide, and as a pH stabilized core having an enteric or delayed release coating which protects captopril until it reaches the colon. Captopril is available for administration in tablet or capsule form. A discussion of the dosage, administration, indications and contraindications associated with captopril and other ACE inhibitors can be found in the *Physicians Desk Reference*, Medical Economics Data Production Co., Montvale, N.J. 2314–2320 (1994).

In an example of an oral therapeutic composition of retinoic acid suitable for treatment of ventricular muscle cell hypertrophy comprises tablets, capsules of hard or soft gelatin methylcellulose, or of another suitable material easily dissolved in the digestive tract. The oral dosages the formulation contains 1% retinoic acid and 99% soft gelatin methylcellulose. In another example of an oral dosage, the formulation contains 20 mg 9-cis retinoic acid and 70 mg gelatin. In an example of an injectable therapeutic composition of retinoic acid, the formulation contains 1% retinoic acid and 99% saline, wherein retinoic acid is the sodium or potassium salt thereof. In another example of an injectable therapeutic composition of retinoic acid, the formulation contains 5% of the potassium salt of retinoic acid, 1% ACE inhibitor captopril, and 94% saline.

The following examples are meant to illustrate, but not to limit, the invention.

EXAMPLE 1

Effect of Retinoic Acid on the Hypertrophic Response of Ventricular Muscle Cells.

The effects of retinoic acid on the hypertrophic response of ventricular muscle cells to the $\alpha_1$-adrenergic agonist phenylephrine (Phe) was studied in a cultured neonatal rat ventricular muscle cell model (Knowlton et al. (1991) J. Biol. Chem. 266:7759–7768; Shubeita et al. (1990) J. Biol. Chem. 265:20555–20562, both references herein specifically incorporated by reference).

Cell Culture Techniques

Neonatal rat ventricular myocytes were prepared and cultured as previously described (Iwaki et al. (1990) J. Biol. Chem. 265:13809–13817, herein specifically incorporated by reference). Briefly, hearts from 1–2 day old Sprague-Dawley rats were recovered, and the ventricular portions dissected and collected. Ventricular cells were dispersed by digestion with collagenase II (Worthington) and pancreatin (GIBCO). Myocytes were purified by centrifugation through Percoll step gradients, resulting in a purification of greater than 95% myocytes (Sen et al. (1988) J. Biol. Chem. 263:19132–19136), and plated at a density of $2\times10^5$ per well of the two well chamber slide precoated with 15 μg/ml laminin, or at a density of $2.5\times10^5$ per well of the 24 well tissue culture plate precoated with 1% gelatin. The cells were cultured overnight in 4:1 Dulbecco's modified Eagles medium/medium 199 (GIBCO), supplemented with 10% fetal bovine serum ("FBS"), and antibiotics (100 U/ml penicillin and 100 μg/ml streptomycin). Cells were then refed with fresh medium containing $4\times10^{-7}$ M of retinoic acid or its agonists (TTNPB or 3-methyl-TTNPB) for at least 10 hours for the pretreatment, then washed 3 times with serum-free medium and cultured in serum-free maintenance media (4:1 Dulbecco's modified Eagles medium/medium 199 with antibiotics) supplemented with phenylephrine (Phe), endothelin, or retinoic acid (RA) alone, or Phe or endothelin with RA for 48–72 hr. Concentrations were Phe, $2\times10^{-5}$ M; endothelin, $1\times10^{-8}$ M; RA, $5\times10^{-7}$ M.

Immunofluorescence Techniques and Morphological Analysis

Indirect immunofluorescence assays were performed as previously described (Iwaki et al. (1990) supra). After a 24 hr attachment, the myocytes were washed 3 times with medium without serum, then cultured in media as described above containing in serum-free media (maintenance media), Phe, Phe and all-trans retinoic acid (RA), RA alone, 10% FBS, or both FBS and RA for 48–72 hr. The cells were rinsed with PBS, then fixed for 15 min at room temperature with 3% paraformaldehyde in 10 mM $NaPO_4$, 150 mM NaCl, 1 mM $MgCl_2$, pH 7.4. The cells were then incubated in 50 mM $NH_4Cl$ for 10 min, washed twice with PBS, then permeabilized with 0.2% Triton X-100 in PBS for 15 min at room temperature, followed by 3 additional PBS washes. The chamber slides were incubated with 1% bovine serum albumin for 10 min to block non-specific sites, incubated with TrpE/MLC-2v antisera (Sen et al. (1988) supra) for 60 min at 37° C., rinsed and washed 4 times with PBS. Subsequently, the chamber slides were incubated for 60 min at 37° C. with FITC-conjugated goat anti-rabbit IgG in PBS, and then rinsed and washed 4 times with PBS. The slides were mounted on glass coverslips with H-1000 Vectashield Mounting Medium (Vecta), viewed and photographed by fluorescence microscopy. Cell images were projected onto paper and individual cells were traced. Individual tracings were cut from the paper and weighted for estimation of cell size.

Results

Cells cultured in maintenance media showed a relatively small cell size, poorly organized myofilaments, and poor contractile ability, whereas cells cultured in the presence of Phe exhibit an altered phenotype, with increased size, well organized myofilaments, and regular contractions. In cells cultured in the presence of Phe and RA, the Phe-stimulated increase in cell size was largely reduced, whereas the myofilaments were still well organized and cells continued to exhibit contractile ability. Cells cultured in the presence of RA alone showed little change in cell phenotype. The hypertrophic response is stimulated by the multiple growth factors present in serum. Retinoic acid had no effect on serum-treated cells.

To more precisely quantitate the effects of RA, multiple fields from independent cultured cell preparations were examined, utilizing a previously described morphometric assay for the hypertrophic phenotype (Knowlton et al. (1993) J. Biol. Chem. 268:15374–15380). Results are summarized in Table 1. Cell size was estimated by measuring the area which individual cells attached on the tissue culture chamber slides. Data is the means±S.E of values from two experiments.

TABLE 1

| Effect of Retinoic Acid on Ventricular Muscle Cell Size | | |
|---|---|---|
| MEDIUM | NUMBER OF CELLS | *RELATIVE CELL SIZE |
| MAINTENANCE | 23 | 100 ± 6 |
| RA $1 \times 10^{-7}$ M | 31 | 140 ± 14 |
| RA $1 \times 10^{-6}$ M | 40 | 120 ± 15 |
| Phe. $5 \times 10^{-6}$ M | 35 | 320 ± 21 |
| Phe. $5 \times 10^{-6}$ M + RA $1 \times 10^{-7}$ M | 39 | 210 ± 20 |

TABLE 1-continued

Effect of Retinoic Acid on Ventricular Muscle Cell Size

| MEDIUM | NUMBER OF CELLS | *RELATIVE CELL SIZE |
|---|---|---|
| Phe. 5 × 10$^{-6}$ M + RA 1 × 10$^{-6}$ M | 31 | 160 ± 17 |
| 10% of FBS | 26 | 300 ± 25 |
| 10% OF FBS + RA 1 × 10$^{-6}$ M | 25 | 290 ± 34 |

EXAMPLE 2
Effect of Retinoic acid on Cardiac Gene Expression

Total RNA was isolated from primary ventricular myocytes cultured in maintenance medium alone (control), or in the presence of 5×10$^{-6}$ M Phe, 5×10$^{-6}$ M Phe and 1×10$^{-6}$ M RA, or 1×10$^{-6}$ M RA alone by the quanidine HCl method (Chirgwin et al. (1979) Biochemistry 18:5294–5299). Northern blot hybridizations were perfomed as described previously (Iwaki et al. (1990) supra). 20 μg of each sample RNA was fractionated by agarose gel electrophoresis and transferred to nylon membranes, and hybridized with radiolabeled cDNA probes of ANF (Glembotski et al. (1987) Endocrinology 12:843–852), myosin light chain-2v (MLC-2v) (Kumar et al. (1986) J. Biol. Chem. 261:2866–2872), tropononin I (TnI) (provided by Dr. S. Evans, University of California, San Diego), and glucose-6-phosphatase dehydrogenase (GADPH). The extent of hybridization was quantitated by densitometry of the corresponding autoradiogram, and normalized to the signals obtained with GADPH to correct for differences in loading and transfer efficiencies. Results are shown in Tables 2 and 3. Cells were also cultured in 0, 10$^{-8}$ M, 10$^{-7}$ M, or 10$^{-6}$ M RA, and probed with radiolabeled ANF and GADPH cDNAs. Results are shown in Table 3.

TABLE 2

Phe and RA Effect on Cardiac RNA Expression

| | Maintenance | Phe | Phe + RA | RA |
|---|---|---|---|---|
| ANF | 0.7 | 4.2 | 1.1 | 0.5 |
| MLC-2v | 0.5 | 0.7 | 1.5 | 0.9 |
| TnI | 2.3 | 1.9 | 2.3 | 1.7 |

TABLE 3

Dose-Dependency of RA Effect on Cardiac RNA Expression

| RA (M) | 0 | 1 × 10$^{-8}$ | 1 × 10$^{-7}$ | 1 × 10$^{-6}$ |
|---|---|---|---|---|
| ANF | 6.6 | 2.5 | 1.5 | 2.1 |

EXAMPLE 3
Transfection Analysis of ANF-Luciferase Fusion Gene in Ventricular Muscle Cells To test the effect of RA on Phe stimulated ANF promoter activity, the following plasmids were used in transient transfection assays: pANF(−3003)LΔ5', the ANF/luciferase fusion gene, composed of a 3003 bp fragment of the ANF 5'-flanking region (Argentin et al. (1985) J. Biol. Chem. 260:4568–4571) which was inserted into the luciferase reporter vector pSVOALΔ5' (de Wet et al. (1987) Mol. Cell. Biol. 7:725–737); pRSVLΔ5' with a RSV promoter fused with luciferase gene, pSVOALΔ5'; a promoterless vector; and pON249 a β-galactosidase expression vector with a CMV promoter (Cherrington et al. (1989) J. Virol. 63:1435–1440).

Neonatal rat ventricular myocytes were prepared and cultured as described above. After 24 hr attachment of primary myocytes in 24 well plates, cells were refed with fresh medium containing 10% FBS for 4 hr, then transfected with 0.65 μg DNA containing 500 ng of pANF(−3003)LΔ5', 50 ng of pON249, and either 50 ng of RA receptor expression vector and 50 ng of inactive control plasmid pSVOALΔ5', or 100 ng of control plasmid, using the standard calcium phosphate method (Gorman et al. (1982) Mol. Cell. Biol. 9:5022–5033). Following overnight incubation, cells were washed 3 times with PBS, then cultured with serum-free maintenance medium (1:-RA-Phe), 2×10$^{-6}$ M Phe (2:-RA+Phe), or 1×10$^{-6}$ M RA+2×10$^{-6}$ M Phe (3:-RA+Phe) and incubated for 48 hr. Cells were washed twice with PBS, then lysed in 100 μl extraction buffer (100 nM KPO$_4$, pH 7.4, 1 mM DTT, 0.5% Triton X-100) on ice for 15 min. 20 μl of each extract was assayed in an Autolumat LB953 (Berthold) with an assay buffer consisting of 100 mM Tricine, 10 mM MgSO$_4$, 2 mM EDTA, 1 mM DTT, 4 mM ATP, 7.5 nM luciferin, pH 7.8. β-galactosidase activity was assayed on 10 μl samples as described previously (Rosenthal (1987) Methods Enzymol. 152:704–720). Luciferase activities were normalized to their corresponding β-galactosidase activities to correct for variation in transfection efficiency. Results are shown in FIG. 1A. Phe induced gene expression was suppressed to control levels in the presence of RA.

Control cells were transfected with a Rous sarcoma virus (RSV) promoter-luciferase gene construct (pRSVLΔ5') and cultured as above. Results are shown in FIG. 1B. Phe induction of gene expression was further enhanced in the presence of RA.

Cells transfected with the ANF promoter-luciferase gene construct were cultured in maintenance medium, 2×10$^{-6}$ M Phe, 1×10$^{-8}$ M endothelin-1, or 10% FBS with and without 1×10$^{-6}$ M RA. Results are shown in FIG. 1C. Phe, endothelin-1, and serum induced gene expression. RA suppressed Phe and endothelin-1 gene expression to control levels; serum-induced gene expression was not suppressed by RA.

EXAMPLE 4
Activity of RA Receptors

To assay for the activity of retinoic acid receptors in cultured ventricular muscle cells, RXR-specific response element CRBP II or RAR-RXR heterodimer-specific response element β-RE I were cloned into an enhancer-dependent heterologous reporter context and introduced by transfection as described in Example 3. The following plasmids were used in transient transfection assays: CMV-hRARα, composed of a CMV promoter and human RARα cDNA (Umesono et al. (1991) Cell 65:1–20); CMV-hRXRα containing CMV promoter and human RXRα cDNA (Mangelsdorf et al. (1990) Nature 345:224–229). The luciferase reporter constructs, CRBP II-luciferase and β-RE I-luciferase, containing retinoic acid response elements were made in a truncated TK promoter context using sequences from the rat CRBP II gene (Mangelsdorf et al. (1991) Cell 66:555–561) or the mouse gene RARβ2 gene (Sucov et al. (1990) Proc. Natl. Acad. Sci. U.S.A. 87:5392–5396) promoters.

Reporter plasmids containing CRBP II-luciferase or β-RE I-luciferase were separately transfected into ventricular myocardial cells without or with co-transfected expression plasmids which contain human RXRα or RARα cDNA driven by a CMV promoter. Ligands, 9-cis (9cRA) (5×10$^{-7}$ M) or all-trans RA (atRA) ($5 \times 10^{-7}$ M), were separately added to the cultures to activate CRBP II or β-RE1 promoters (Heyman et al. (1992) supra).

Results

The effects of 9cRA or atRA on the promoter activities are shown in FIG. 2A. The CRBP II reporter construct was not activated by endogenous receptors in the presence of 9cRA, but was up-regulated when co-transfected with an RXR-expression construct. The β-RE heterodimer reporter gene was functional in the presence of atRA using the endogenous complement of receptors, and this activity was further increased by co-transfection of receptor expression constructs.

EXAMPLE 5

Effect of Dominant Negative RA Receptor on Gene Expression

The reporter construct containing the ANF promoter was transfected alone or with a dominant negative reporter construct (CMV-hRAR403), or the wild type receptor construct, CMV-hRXR, or CMV-hRAR into ventricular myocardial cells cultured in Phe ($2 \times 10^{-6}$ M) containing medium with or without atRA ($1 \times 10^{-7}$ M). The dominant negative hRARα cDNA, a carboxy-terminal truncation at amino acid 403 referred to as hRARα403, has been previously described (Damm et al. (1993) Proc. Natl. Acad. Sci. U.S.A. 90:2989–2993), and is expressed from the CMV promoter.

In the presence of the dominant negative mutant receptor, RA did not suppress Phe induction of gene expression from the ANF promoter construct (FIG. 2B).

EXAMPLE 6

Effect of RA Receptor-Specific Synthetic Retinoids on Phe Induction of Expression Ventricular cells were transfected and with the ANF-luciferase reporter gene and activated by $2 \times 10^{-6}$ M Phe with a series of concentrations of three agonists; LG64, TTNPB, and 3-methyl-TTNPB. 9-cis retinoic acid, TTNPB, 3-methyl TTNPB, and LG64 were provided by Dr Richard Heyman (Ligand Pharmaceuticals). All compounds were diluted at least 1:1000 in tissue culture media.

The effects of LG64, 3TTNPB, and TTNPB on relative luciferase activity are shown in FIG. 3A. TTNPB and 3-methyl-TTNPB are equivalent in their potency to block induction of the ANF promoter, whereas the RXR-selective compound LG64 is approximately 40-fold less potent in this assay.

EXAMPLE 7

Effect of Hormones on Phe-Induced Gene Expression

Cultured cardiomyocytes were transfected with the ANF promoter reporter construct and co-cultured with $2 \times 10^{-7}$ M Phe and one of the following: dexamethasone (Dex), thyroid hormone (T3), 17β-estradiol (E2), 1,25-dihydroxy-vitamin D (D3), linoleic acid (LA), and RA (each present in a concentration of $1 \times 10^{-7}$ M). Phe (Sigma) was dissolved in maintenance medium and filtered through a 0.22 μm (diameter) membrane. All-trans RA was dissolved in a small amount of DMSO, then diluted with 100% EtOH. Dex, E2, and T3 (all from Sigma) were dissolved in 100% EtOH. D3 and LA were provided by Dr. Barry Forman (Salk Institute) dissolved in EtOH. All compounds were diluted to at least 1:1000 in tissue culture medium. As shown in FIG. 3B, only treatment with RA prevented the induction of the ANF promoter. Treatment with thyroid hormone, estrogen, and vitamin D were inactive in this assay, and dexamethasone (a synthetic glucocorticoid) actually increased ANF expression.

EXAMPLE 8

Testing for In Vivo Suppression of Ventricular Muscle Cell Hypertrophy

A. Normal Rats. A purified retinoic acid compound to be tested for suppression of ventricular muscle cell hypertrophy is administered to normal rats, and its effect on cardiovascular parameters such as blood pressure, heart rate, systemic vascular resistance, contractility, force of heart beat, concentric or dilated hypertrophy, left ventricular systolic pressure, left ventricular mean pressure, left ventricular systolic pressure end-diastolic pressure, cardiac output, stroke index, histological parameters, and ventricular size and wall thickness.

B. Pressure-Overload Mouse Model. A purified retinoic acid compound is also tested in the pressure-overload mouse model wherein the pulmonary artery is constricted, resulting in right ventricular failure.

C. RV Murine Dysfunctional Model. A retroviral murine model of ventricular dysfunction can be used to test the ability of a purified retinoic acid compound to suppress ventricular muscle cell hypertrophy, by assaying dP/dt, ejection fraction, and volumes with the above-described hypertrophy assay. In this model, the pulmonary artery of the mouse is constricted so as to generate pulmonary hypertrophy and failure.

D. Transgenic Mouse Model. Transgenic mice that harbor a muscle actin promoter-IGF-I fusion gene display cardiac and skeletal muscle hypertrophy, without evidence of myopathy or heart failure. IGF-I-gene-targeted mice display defects in cardiac myogenesis (as well as skeletal), including markedly decreased expression of ventricular muscle contractile protein genes. Purified retinoic acid compounds are tested in these two models.

Additionally, genetic-based models of dilated cardiomyopathy and cardiac dysfuntion, without necrosis, can be developed in transgenic and gene-targeted mice (MLC-ras mice; aortic banding of heterozygous IGF-I-deficient mice). Another useful animal models are the RXRα mutant mouse model (Sucov et al. (1994) Genes Dev. 8:1997–1018) and RXRα-/-embryo model (Dyson et al. (1995) Proc. Natl. Acad. Sci. (In Press)). These genetically-based animal models display important features of ventricular chamber dysmorphogenesis.

E. Post-Myocardial Infarction Rat Model. A purified retinoic acid compound is also tested in a post-myocardial infarction rat model, which is predictive of human congestive heart failure in producing ANF. Male Sprague-Dawley (Charles River Breeding Laboratories, Inc., eight weeks of age) are acclimated to the facility for at least one week before surgery. Rats are fed a pelleted rat chow and water ad libitum and housed in a light- and temperature-controlled room.

Coronary arterial Ligation

Myocardial infarction is produced by left coronary arterial ligation as described by Greenen et al. (1987) J. Appl. Physiol. 93:92–96 and Buttrick et al. (1991) Am. J. Physiol. 260:11473–11479. The rats are anesthetized with sodium pentobarbital (60 mg/kg, intraperitoneally), intubated via tracheotomy, and ventilated by a respirator. After a left-sided thoracotomy, the left coronary artery is ligated approximately 2 mm from its origin with a 7-0 silk suture. Sham animals undergo the same procedure except that the suture is passed under the coronary artery and then removed. All rats are handled according to the "Position of the American Heart Association on Research Animal Use" adopted Nov. 11, 1984, by the American Heart Association. Four to six weeks after ligation, myocardial infarction could develop into heart failure in rats. The congestive heart failure in this model reasonably mimics congestive heart failure in most human patients.

Electrocardiograms

One week after surgery, electrocardiograms are obtained under light metofane anesthesia to document the development of infarcts. The ligated rats are subgrouped according to the depth and persistence of pathological Q waves across the precordial leads (Buttrick et al. (1991) supra; Koner et al. (1983) Am. Heart J. 51:1009–1013). This provides a gross estimate of infarct size and assures that large and small infarcts are not differently distributed in the ligated rats treated with a retinoic acid compound and vehicle. Confirmation is made by precise infarct size measurement.

Administration of a Retinoic Acid Compound

Four weeks after surgery, a test retinoic acid compound (5 $\mu$g/kg to 50 mg/kg twice a day for 15 days) or saline vehicle is injected subcutaneously in both ligated rats and sham controls. Body weight is measured twice a week during treatment. The test retinoic acid compound is administered in saline or water as a vehicle.

Catheterization

After 13-day treatment with the test retinoic acid compound or vehicle, rats are anesthetized with pentobarbital sodium (50 mg/kg, intraperitoneally). A catheter (PE 10 fused with PE 50) filled with heparin-saline solution (50 U/ml) is implanted into the abdominal aorta through the right femoral artery for measurement of arterial pressure and heart rate. A second catheter (PE 50) is implanted into the right atrium through the right jugular vein for measurement of right atrial pressure and for saline injection. For measurement of left ventricular pressures and contractility (dP/dt), a third catheter (PE 50) is implanted into the left ventricle through the right carotid artery. For the measurement of cardiac output by a thermodilution method, a thermistor catheter (Lyons Medical Instrument Co., Sylmar, Calif.) is inserted into the aortic arch. The catheters are exteriorized at the back of the neck with the aid of a stainless-steel wire tunneled subcutaneously and then fixed. Following catheter implantation, all rats are housed individually.

Hemodynamic Measurements

One day after catherization, the thermistor catheter is processed in a microcomputer system (Lyons Medical Instrument, Co.) for cardia output determination, and the other three catheters are connected to a Model CP-10 pressure transducer (Century Technology Company, Inglewood, Calif.) coupled to a Grass Model 7 polygraph (Grass Instrumentation, Quincy, Mass.). Mean arterial pressure (MAP), systolic arterial pressure (SAP), heart rate (HR), right atrial pressure (RAP), left ventricular systolic pressure (LVSP), left ventricular mean pressure (LVMP), left ventricular end-diastolic pressure (LVEDP), and left ventricular maximum (dP/dt) are measured in conscious, unrestrained rats.

For measurement of cardiac output, 0.1 ml of isotonic saline at room temperature is injected as a bolus via the jugular vein catheter. The thermodilution curve is monitored by VR-16 simultrace recorders (Honeywell Co., N.Y.) and cardiac output (CO) is digitally obtained by the microcomputer. Stroke volume (SV)=CO/HR; cardiac index (CI)=CO/BW; systemic vascular resistance (SVR)=MAP/CI.

After measurement of these hemodynamic parameters, 1 ml of blood is collected through the arterial catheter. Serum is separated and stored at −70° C. for measurement of retinoic acid compound levels and other biochemical parameters of interest.

The rats are then anesthetized with pentobarbital sodium (60 mg/kg) and the heart arrested in diastole with an intra-atrial injection of KCl (1 M). The heart is removed, and the atria and great vessels are trimmed from the ventricle. The ventricle is weighed and fixed in 10% buffered formalin.

Infarct Size Measurements

The right ventricular free wall is dissected from the left ventricle. The left ventricle is cut in four transverse slices from apex to base. Five micrometer sections are cut and stained with Massons' trichrome stain and mounted. The endocardial and epicardial circumferences of the infarcted and non-infarcted left ventricle are determined with a planimeter Digital Image Analyzer. The infarcted circumference and the left ventricular circumference of all four slices are summed separately for each of the epicardial and endocardial surfaces and the sums are expressed ass a ratio of infarcted circumference to left ventricular circumference for each surface. These two ratios are then averaged and expressed as a percentage for infarct size.

Statistical Analysis

Results are expressed as mean±SEM. Two-way and one-way analysis of variance (ANOVA) is performed to assess differences in parameters among groups. Significant differences are then subject to post hoc analysis using the Newman-Keuls method. P<0.05 is considered significant.

Results

The mean body weight before and after treatment with the test retinoic acid compound or vehicle is not expected to be different among the treatment groups. It is expected that the administration of a retinoic acid compound to the ligated rats in the doses set forth above will result in improved cardiac hypertrophy and improved cardiac function in congestive heart failure.

It would be reasonably expected that the rat data may be extrapolated to horses, cows, humans, and other mammals, correcting for the body weight of the mammal in accordance with recognized veterinary and clinical procedures. Using standard protocols and procedures, the veterinarian or clinician will be able to adjust the doses, scheduling, and mode of administration of the retinoic acid compound to achieve maximal effects in the desired mammal being treated. Humans are expected to respond in this manner as well.

EXAMPLE 9

Treatment of Dilated Cardiomyopathy in Human Patients

Intervention

Patient self-administration of a retinoic acid compound or at an initial dose of 10–150 $\mu$g/kg/day is proposed. The dose would be adjusted downward for adverse effects. If no beneficial effect and no limiting adverse effects are determined at the time of re-evaluation, the dose would be adjusted upward. Concurrent medication doses (e.g., captopril as an ACE inhibitor and diuretics) would be adjusted at the discretion of the care provider. After the maximum dose is administered for 8 weeks, the retinoic acid compound administration is stopped, and re-evaluation performed after a similar time period off treatment (or a placebo).

Inclusion Criteria

Patients would be considered for inclusion in the study if the meet the following criteria: (1) dilated cardiomyopathy (DCM), idiopathic DCM, or ischemic DCM without discrete areas of akinesis/dyskineses of the left ventricle (LV) on contrast ventriculography or 2D echocardiography. Evidence for impaired systolic function to include either LV end-diastolic dimension (EDD)>3.2 cm/m$^2$ BSA or EDV>82 ml/m$^2$ on 2D echocardiography, LV fractional shortening<28% on echocardiography, or ejection fraction (by contrast ventriculography or radionuclide angiography) <0.49; (2) Symptoms: New York Heart Association class III or peak exercise VO$_2$<16 ml/kg/min (adjusted for age), stable for at least one month on digoxin, diuretics, and vasodilators (ACE inhibitors); (3) Concurrent ACE inhibitor therapy; (4) Adequate echocardiographic "windows" to permit assessment of left ventricular volume and mass; (5) Ability to self-administer a retinoic acid compound according to dosage schedule and to return reliably for follow-up assessments; (6) consent of patient and patient's primary physician to participate; and (7) absence of exclusion criteria.

Exclusion Criteria

Patient would be excluded from consideration for any of the following reasons: dilated cardiomyopathy resulting from valvular heart disease (operable or not), specific treatable etiologies (including alcohol, if abstinence has not been attempted), or operable coronary artery disease; exercise limited by chest pain or obstructive peripheral vascular disease; chronic obstructive lung disease; diabetes mellitus or impaired glucose tolerance; history of carpal tunnel syndrome or evidence for positive Tinel's sign on examination; history of kidney stones; symptomatic osteoarthritis; inability to consent or participate in serial bicycle ergometry with invasive hemodynamic monitoring (described below); or active malignancy.

Patient Assessment (1) Major assessment point: baseline; after peak stable retinoic acid compound dose maintained for 8 weeks; after equal period after drug discontinuation. It is anticipated that patients would remain in the hospital for 2–3 days at the onset of active treatment, with daily weights and laboratory data including electrolytes, phosphorus, BUN, creatinine, and glucose. Following this, they would be monitored for daily for 2–3 additional days by (1) physical examination, (2) symptom point score (Kelly et al. (1990) Amer. Heart J. 119:1111), (3) laboratory data (CBC; electrolytes including $Mg^{+2}$ and $Ca^{+2}$; BUN; creatinine; phosphorus; fasting glucose and lipid profile including total cholesterol, HDL-C, LDL-C, triglycerides; liver function tests such as AST, ALT, alkaline phosphatase, total bilirubin; total protein; albumin; uric acid; and retinoic acid compound), (4) 2D, M-mode, and doppler echocardiography, including diastolic and systolic dimensions at the papillary muscle level, ejection fraction estimate by area planimetry from apical 2-chamber and 4-chamber views, estimated systolic and diastolic volumes by Simpson's rule method, and estimated left ventricular mass, doppler assessment of mitral valve inflow profile (IVRT, peak E, peak A, deceleration time, A wave duration), and pulmonary vein flow profile (systolic flow area, diastolic flow ara, A reversal duration, and velocity), (5) rest and exercise hemodynamics and measured oxygen consumption, using bicycle ergometry with percutaneously inserted pulmonary artery and arterial catheters. Perceived exertion level would be scored on the Borg scale, and measurements of pulmonary artery systolic, diastolic, and mean pressures, as well as arterial pressures and pulmonary capillary wedge pressure would be measured at each increment of workload, along with arterial and mixed venous oxygen content for calculating cardiac output, (6) assessment of body fat and lean body mass, as well as skeletal muscle strength and endurance.

Weekly interim assessment points would include physical examination, symptom point score, and laboratory data.

Although the invention has been described with reference to the presently preferred embodiments, it should be understood that various modifications can be made without departing from the spirit of the invention. Accordingly, the invention is limited only by the following claims.

What is claimed is:

1. A therapeutic method for treatment or prevention of ventricular muscle cell hypertrophy-related heart failure in a mammal, comprising administering to a patient in need thereof a therapeutically effective amount of a retinoic acid compound, wherein said retinoic acid compound is a compound having the general formula

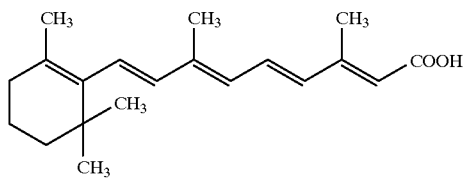

or derivatives, and pharmaceutical salts thereof, said compound characterized by ability to bind a retinoic acid receptor and suppress ventricular muscle cell hypertrophy.

2. The therapeutic method of claim 1 wherein said heart failure is mediated by an $\alpha_1$-adrenergic agonist.

3. The therapeutic method of claim 1 wherein said heart failure is mediated by an endothelin.

4. The method of claim 1, wherein said retinoic acid compound is selected from the group consisting of all-trans retinoic acid, 9-cis retinoic acid, TTNPB, and 3-methyl-TTNPB, or a pharmaceutical salt thereof.

5. The method of claim 2, wherein said pharmaceutical salt is potassium or sodium.

6. The method of claim 1, wherein said ventricular muscle cells are human cells.

7. The method of claim 6, wherein said human cells are present in a living human heart.

8. A therapeutic formulation for treatment or prevention of ventricular muscle cell hypertrophy, comprising a therapeutically effective amount of a retinoic acid compound and one or more pharmaceutically acceptable excipients, wherein said retinoic acid compound is a compound having the general formula

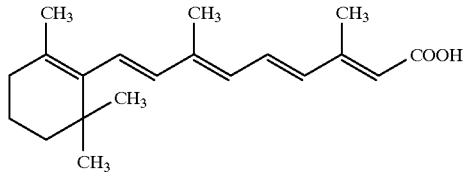

or derivatives, and pharmaceutical salts thereof, said compound characterized by ability to bind a retinoic acid receptor and suppress ventricular muscle cell hypertrophy.

9. The formulation of claim 8 further comprising at least one compound selected from the group consisting of an inhibitor of angiotensin-converting enzyme (ACE), an endothelin receptor antagonist, a β-adrenoceptor antagonist, an $\alpha_1$-adrenoceptor antagonist, an anti-oxidant, and growth hormone.

10. The formulation of claim 8, wherein said retinoic acid compound is selected from the group consisting of all-trans retinoic acid, 9-cis retinoic acid, TTNPB, and 3-methyl-TTNPB, or a pharmaceutical salt thereof.

11. The formulation of claim 10 wherein said pharmaceutical salt is potassium or sodium.

12. The formulation of claim 10, wherein said retinoic acid compound is present in the amount of about 1 to 10% by weight and said excipient(s) is present in the amount of about 80 to 99% by weight.

13. The formulation of claim 9 wherein said ACE inhibitor is present in the amount of about 1 to 10% by weight.

* * * * *